US012607696B2

(12) United States Patent
Jeong et al.

(10) Patent No.: US 12,607,696 B2
(45) Date of Patent: Apr. 21, 2026

(54) SYSTEMS AND METHODS FOR SIMULTANEOUSLY MEASURING DIFFUSION WEIGHTED SPIN-ECHO AND STIMULATED ECHO SIGNALS

(71) Applicant: UNIVERSITY OF UTAH RESEARCH FOUNDATION, Salt Lake City, UT (US)

(72) Inventors: Eun-Kee Jeong, Salt Lake City, UT (US); Kyle Jeong, Salt Lake City, UT (US); John W. Rose, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 503 days.

(21) Appl. No.: 17/989,096

(22) Filed: Nov. 17, 2022

(65) Prior Publication Data

US 2023/0152407 A1 May 18, 2023

Related U.S. Application Data

(60) Provisional application No. 63/289,235, filed on Dec. 14, 2021, provisional application No. 63/280,366, filed on Nov. 17, 2021.

(51) Int. Cl.
*G01R 33/563* (2006.01)
*A61B 5/055* (2006.01)
(Continued)

(52) U.S. Cl.
CPC ........ *G01R 33/56341* (2013.01); *A61B 5/055* (2013.01); *G01R 33/5608* (2013.01); *G01R 33/5616* (2013.01)

(58) Field of Classification Search
CPC .......... G01R 33/56341; G01R 33/5608; G01R 33/5616; G01R 33/5615; A61B 5/055
See application file for complete search history.

(56) References Cited

U.S. PATENT DOCUMENTS 8,143,889 B2 3/2012 Jeong et al.
8,503,752 B2 8/2013 Feiweier
(Continued)

OTHER PUBLICATIONS

Shi, Xianfeng, Seong-Eun Kim, and Eun-Kee Jeong. "Single-shot T1 mapping using simultaneous acquisitions of spin-and stimulated-echo-planar imaging (2D ss-SESTEPI)." Magnetic resonance in medicine 64.3 (2010): 734-742. (Year: 2010).*
(Continued)

*Primary Examiner* — Rishi R Patel
(74) *Attorney, Agent, or Firm* — Ballard Spahr LLP

(57) ABSTRACT

A method for applying a diffusion-weighting gradient during acquisition of diffusion-weighted imaging signals from a selected portion of a nervous system of a subject. Planar diffusion-weighted spin-echo (DWSE) imaging signals and planar diffusion-weighted stimulated-echo (DWSTE) imaging signals can be obtained to provide a plurality of sets of imaging signals. At least one set of imaging signals includes DWSTE signals that are associated with a high-b-value. A signal difference between DWSE imaging signals and DWSTE imaging signals can be corrected based on respective sets of DWSE imaging signals and DWSTE imaging signals having b-values at or near zero.

20 Claims, 10 Drawing Sheets

(51) Int. Cl.
    *G01R 33/56*         (2006.01)
    *G01R 33/561*       (2006.01)

(56)            References Cited

U.S. PATENT DOCUMENTS

| | | |
|---|---|---|
| 9,770,186 B2 | 9/2017 | Jeong et al. |
| 10,551,458 B2 | 2/2020 | Tan et al. |
| 10,959,642 B2 | 3/2021 | Jeong et al. |
| 2018/0049665 A1* | 2/2018 | Jeong ..................... A61B 5/055 |
| 2021/0096205 A1 | 4/2021 | Kettinger et al. |

OTHER PUBLICATIONS

Bornert, P.; Jensen, D. Single-Shot-Double-Echo EPI.Magn Reson Imaging 1994, 12 (7), 1033-1038.

Franconi, F.; Sonier, C. B.; Seguin, F.; Le Pape, A.; Akoka, S. Acquisition of Spin Echo and Stimulated Echo by a Single Sequence: Application to MRI of Diffusion. Magn. Reson. Imaging 1994, 12 (4), 605-611.

Shi, X.; Jeong, E. Single-Shot T1 Mapping Using Simultaneous Acquisitions of Spin- and Stimulated-Echo-Planar Imaging (2D Ss-SESTEPI). Magn Reson Med 2010, 64 (3), 734-742.

Sapkota, N.; Yoon, S.; Thapa, B.; Lee, Y.; Bisson, E.; Bowman, B.; Miller, S.; Shah, L.; Rose, J.; Jeong, E. Characterization of Spinal Cord White Matter by Suppressing Signal from Hindered Space. A Monte Carlo Simulation and an Ex Vivo Ultrahigh-b Diffusion-Weighted Imaging Study. J. Magn. Reson. 2016, 272, 53-59.

Thapa, B.; Sapkota, N.; Lee, Y.; Jeong, K.; Rose, J.; Shah, L. M.; Bisson, E.; Jeong, E. K. Ultra-High-b Radial Diffusion-Weighted Imaging (UHb-RDWI) of Human Cervical Spinal Cord. J. Magn. Reson. Imaging 2019, 49 (1), 204- 211.

Jeong, K. E.; Shah, L. M.; Lee, S. Y.; Thapa, B.; Sapkota, N.; Bisson, E. F.; Carlson, N. G.; Jeong, E. K.; Rose, J. W. High-b Diffusivity of MS Lesion in Cervical Spinal Cord Using Ultrahigh-b DWI (UHb-DWI). NeuroImage: Clinical 2021, 30, 102619.

Sapkota, N.; Shi, X.; Shah, L. M.; Bisson, E. F.; Rose, J.; Jeong, E. Two-Dimensional Single-Shot Diffusion-Weighted Stimulated EPI with Reduced FOV for Ultrahigh-b Radial Diffusion-Weighted Imaging of Spinal Cord. Magn. Reson. Med. 2016, 77 (6), 2167-2173.

Jeong, E. K.; Kholmovski, E. G.; Parker, D. L. High-Resolution DTI of a Localized vol. Using 3D Single-Shot Diffusion-Weighted STimulated Echo-Planar Imaging (3D Ss-DWSTEPI). Magn Reson Med 2006, 56 (6), 1173-1181.

Jeong, E. K.; Guo, J.; Kholmovski, E. G.; Parker, D. L. High-Resolution DTI with 2D Interleaved Multislice Reduced FOV Single-Shot Diffusion-Weighted Epi (2D Ss-RFOV-DWEPI). Magn Reson Med 2005, 54 (6), 1575-1579.

Jeong, K. E.; Lee, S. Y. J.; Yeom, S. K.; Carlson, N. G.; Shah, L. M.; Rose, J. W.; Jeong, E. K. Ultrahigh-b DWI (UHb-DWI) for Quantitative Evaluation of Myelination in Shiverer Mouse Spinal Cord. Magn Reson Med 2021, in-print, PMID: 34418157 DOI: 10.1002/mrm.28978. https://doi.org/10.1002/mrm.28978.

Sapkota, N.; Shi, X.; Shah, L. M.; Bisson, E. F.; Rose, J. W.; Jeong, E. K. E. K.; Guo, J.; Kholmovski, E. G.; Parker, D. L. High-Resolution DTI with 2D Interleaved Multislice Reduced FOV Single-Shot Diffusion-Weighted Epi (2D Ss-RFOV-DWEPI). Magn Reson Med. 2016, pp. 1575-1579. https://doi.org/10.1002/mrm.26302.

* cited by examiner

SYSTEMS AND METHODS FOR SIMULTANEOUSLY MEASURING DIFFUSION WEIGHTED SPIN-ECHO AND STIMULATED ECHO SIGNALS

CROSS-REFERENCE TO RELATED APPLICATIONS

This application claims the benefit of the filing dates of U.S. Provisional Application No. 63/280,366, filed Nov. 17, 2021, and U.S. Provisional Application No. 63/289,235, filed Dec. 14, 2021, the entirety of each of which is hereby incorporated by reference herein.

GOVERNMENT SUPPORT CLAUSE

This invention was made with government support under grant NS106097 awarded by the National Institutes of Health. The government has certain rights in this invention.

FIELD

This disclosure relates generally to systems and methods for acquiring and relating diffusion-weighted stimulated spin-echo and stimulated echo signals.

BACKGROUND

Quantitative evaluation of spinal cord or optic nerve is important for patient care, particularly for early detection of pathologic change, monitoring the drug treatment in patients (e.g., Multiple Sclerosis patients) and prognostic evaluations in patients (e.g., cervical spondylotic myelopathy patients). Magnetic resonance imaging (MRI) systems can, with a sufficiently high b-value, assist in detecting demyelination, wherein the b-value of an MRI reflects the strength and timing of the gradients used to generate diffusion-weighted images. Conventional magnetic resonance imaging MRI systems are unable to achieve b-values above 3000 s/mm$^2$ and, therefore, are unable to obtain images for detecting demyelination.

Conventionally, to achieve UHb-DWI with b~10,000 s/mm$^2$ on a clinical MRI system with $G_{max}$=40 mT/m, the mixing time, TM, is varied up to 450 ms and permute slice ordering within the long TM to improve the time-efficiency of the measurement. This requires removing the varying $T_1$ decay effect from the DWSTE data and resulting in unreliable data with low signal-to-noise ratio (SNR), particularly for b>5,000 s/mm$^2$.

Still further, MRI systems that are able to achieve b-values above 3000 s/mm$^2$ require sequential collection of diffusion-weighted spin echo (DWSE) and diffusion-weighted stimulated echo (DWSTE). Ability to simultaneously obtain DWSE and DWSTE would, therefore, cut data collection time in half. Because movement of a patient during magnetic resonance imaging can diminish or destroy image quality, decrease in data collection time can improve image quality.

Accordingly, reduced MRI time, improved image quality, and other advantages are provided with the systems and methods disclosed herein.

SUMMARY

Disclosed herein are methods for using at least one processing unit of an MRI system to apply a diffusion-weighting gradient during acquisition of diffusion-weighted imaging signals from a selected portion of a nervous system of a subject. Planar diffusion-weighted spin-echo (DWSE) imaging signals and planar diffusion-weighted stimulated-echo (DWSTE) imaging signals can be simultaneously obtained from the MRI system to provide a plurality of sets of imaging signals. The plurality of sets of imaging signals can comprise a first set of DWSE imaging signals associated with a first low-b-value that is at or near zero, a first set of DWSTE imaging signals associated with a second low-b-value at or near zero, and a second set of DWSTE signals that are associated with a high-b-value. A signal difference between the DWSE imaging signals and the DWSTE imaging signals can be corrected based on the first set of DWSE imaging signals and the first set of DWSTE imaging signals.

In one aspect, a system comprises a magnetic resonance imaging (MRI) system. The MRI system can be configured to apply a diffusion-weighting gradient during acquisition of diffusion-weighted imaging signals from a selected portion of a nervous system of a subject. The MRI system can further be configured to obtain, simultaneously from the MRI system, planar diffusion-weighted spin-echo (DWSE) imaging signals and planar diffusion-weighted stimulated-echo (DWSTE) imaging signals to provide a plurality of sets of imaging signals. The plurality of sets of imaging signals comprise a first set of DWSE imaging signals associated with a first low-b-value that is at or near zero, a first set of DWSTE imaging signals associated with a second low-b-value at or near zero, and a second set of DWSTE signals that are associated with a high-b-value. The system can further comprise a memory and at least one processor in communication with the memory. The memory comprises instructions that, when executed by the at least one processor, cause the processor to correct a signal difference between the DWSE imaging signals and the DWSTE imaging signals based on the first set of DWSE imaging signals and the first set of DWSTE imaging signals.

In one aspect, a computing device can comprise a memory and at least one processor in communication with the memory. The memory comprises instructions that, when executed by the at least one processor, cause the processor to correct a signal difference between the DWSE imaging signals and the DWSTE imaging signals based on the first set of DWSE imaging signals and the first set of DWSTE imaging signals.

DESCRIPTION OF THE DRAWINGS

These and other features of the preferred embodiments of the invention will become more apparent in the detailed description in which reference is made to the appended drawings wherein.

DETAILED DESCRIPTION

Figure 1:
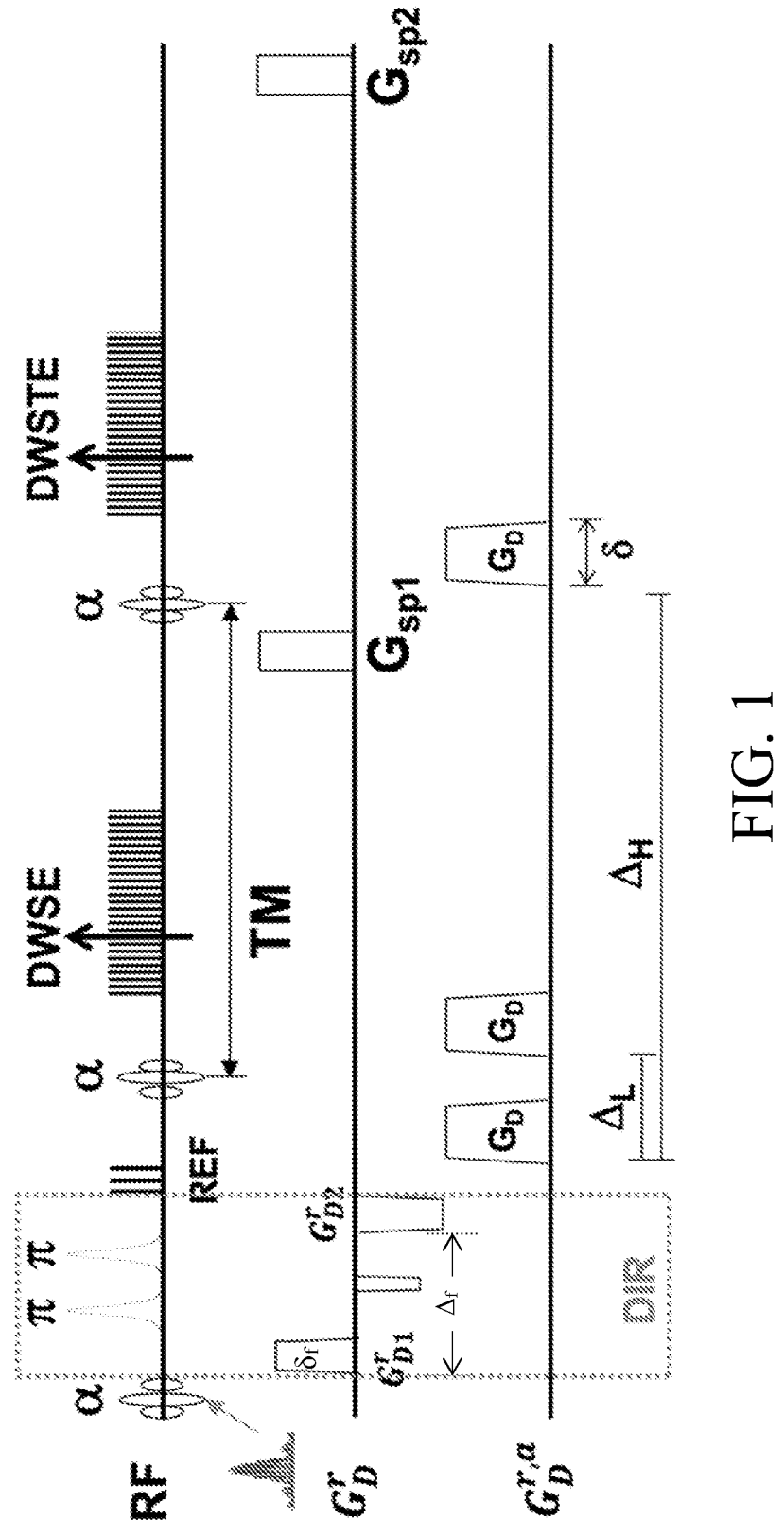
FIG. 1 is a pulse sequence diagram of 2D singleshot DWSESTE-rFOV to acquire interleaved DW-SEPI and DW-STEPI. Reduced-FOV (rFOV) along phase-encoding direction, which is crucial to reduce the geometric distortion for CSC DWI, is accomplished using either 2D RF pulse (arrow) or double-inversion (with two 180° pulses) with appropriate crusher gradients. Ideally, the flipangle α is 90° at position $\vec{r}$.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned or cited herein (including those within the provided reference lists) are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

Further, the dates of publication provided herein can be different from the actual publication dates, which can require independent confirmation.

As used in the specification and the appended claims, the singular forms "a," "an," and the plural referents unless the context clearly dictates otherwise. For example, "a pixel" should be understood to include one or more pixels, and so forth.

As used herein, the word "or" can mean any one member of a particular list but, except where otherwise indicated, can, in other aspects, also include any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

Optionally, in some aspects, when values are approximated by use of the antecedents "about," "substantially," "approximately," or "generally," it is contemplated that values within up to 15%, up to 10%, up to 5%, or up to 1% (above or below) of the particularly stated value or characteristic can be included within the scope of those aspects.

Introduction

The stimulated-echo (STE) pulse sequence is often used to investigate molecular transport, such as molecular translational diffusion[1-3]. The major advantage of STE for diffusion-weighted MRI (DWSTE) is its capability for high-b DWI with long mixing time TM (time between the second and third RF pulses in STE pulse sequence) and relatively short duration of the diffusion gradient pulse. The increased mixing time is valuable to increase the sensitivity of the UHb-DWI to the water exchange at the myelin sheath, which can be used to estimate the water permeability at the myelin sheath[4-6]. Note that conventional DWI using diffusion-weighted spin-echo EPI at the wholebody MRI system is not suitable for ultrahigh-b diffusion-weighted MR image (UHb-DWI), because of excessive signal loss due to a long TE that is resulted from large b values with a limited gradient strength. Therefore, high-b DW imaging can be achieved using a long mixing-time (TM) and short duration of diffusion gradient. To achieve UHb-DWI (e.g., with b~10,000 s/mm$^2$) on a clinical MRI system with $G_{max}$=40 mT/m, one may vary the mixing time TM up to 450 ms and permute slice ordering within the long TM to improve the time-efficiency of the measurement[5,7]. This method requires removing the varying $T_1$ decay effect from the DWSTE data and resulting in unreliable data with low SNR, such as in b>5,000 s/mm$^2$. Fortunately, on modern MRI systems with improved gradient performance, such as with $G_{max}$=80 mT/m, DWI of b~10,000 s/mm$^2$ can be obtained using DWSTE with a fixed TM (~100 ms).

In STE, the transverse magnetization, which can be dephased by the first diffusion-gradient, can be decomposed by the second 90° RF (tipup) pulse into two components: 1) the longitudinal component, which is half the magnitude of the prepared magnetization, and 2) the transverse component, which is the same magnitude. The transverse component is discarded in the conventional STE NMR/MRI[8-10]. This results in wasting of a quadrature component of the magnetization. This half magnetization can be used by measuring a spin-echo after the second 90° RF pulse while simultaneously measuring the stimulated-echo[11-13]. Ideally with perfect 90° flipangles for all three RF pulses in STE and without any other signal decay, such as $T_1$ decay during mixing time, the fraction of the measured spin-echo should be 0.5. In reality, however, it deviates from 0.5 mainly due to the imperfect 90° flipangle of the second RF pulse in STE. Therefore, for successful combination of SE and STE, the effect of imperfect 90° must be corrected, as in previous report for simultaneous acquisitions of DWSE and DWSTE[12] and singleshot $T_1$ mapping[13].

Disclosed herein is method a to obtain DWSE and DWSTE simultaneously with simple RF correction (DW-SESTE) that corrects the difference in signal intensities in DWSE and DWSTE caused by an imperfect 90° pulse, $T_1$ decay during the mixing-time TM, and diffusion weighting effect due to the imaging gradients such as crusher gradients surrounding the second and third RF pulses. In one example, a reduced field-of-view (rFOV) was implemented using two adiabatic full passage (AFP) pulses with appropriate crusher gradient. 2D singleshot DW-SESTE (2D ss-DWSESTE-rFOV) can be applied to a healthy volunteer to demonstrate its capability for UHb-DWI for human cervical spinal cord (CSC). A set of low-b DWSE images were used for conventional diffusion tensor imaging (DTI) and diffusion kurtosis imaging (DKI) analysis and estimate the conventional ADCs and kurtosis along radial ($K_r$) and axial ($K_a$) directions, and fractional anisotropy FA was estimated using $ADC_r$ and $ADC_a$, assuming a cylindrical symmetry.

Systems and Methods

According to some aspects, a plurality of DWSE imaging signals and DWSTE imaging signals can be simultaneously generated. The DWSE imaging signals and DWSTE imaging signals can be stored in sets (e.g., matrices having different DWSE/DWSTE imaging signals at different spatial locations). Each set can be associated with a b-value and is either DWSE or DWSTE. The imaging signals of any given set can be associated with a grayscale shade (or color) in order to convert the set of imaging signals to an image.

Using a set of DWSE imaging signals obtained with b~0 and a set of DWSTE imaging signals obtained with b~0, a correction matrix can be created, the matrix comprising, at each pixel location, a ratio of an imaging signal of the set of DWSE imaging signals with b~0 to an imaging signal of the set of DWSTE imaging signals with b~0.

Every set of DWSTE imaging signals can be multiplied by the correction matrix to scale the sets of DWSTE imaging signals to match the sets of DWSE imaging signals. For example, each imaging signal (e.g., a signal intensity of an imaging pixel) of a set of imaging signals (e.g., DWSTE imaging signals) can be multiplied by the respective ratio of the corresponding pixel of the correction matrix to provide a corrected value, and the corrected values can be provided in a corrected DWSTE matrix. In the alternative, every set of DWSE imaging signals can be multiplied by the inverse of the correction matrix to scale the sets of DSTE imaging signals to the sets of DWSTE imaging signals).

In one aspect, a method can comprise using at least one processing unit of an MRI system to apply a diffusion-weighting gradient during acquisition of diffusion-weighted imaging signals from a selected portion of a nervous system of a subject.

Planar diffusion-weighted spin-echo (DWSE) imaging signals and planar diffusion-weighted stimulated-echo (DWSTE) imaging signals can be simultaneously obtained from the MRI system to provide a plurality of sets of imaging signals. As used herein, except where otherwise indicated, "simultaneous" and "simultaneously" refer to obtaining a respective DWSE imaging signal and DSWTE imaging signal within the same MRI acquisition pulse sequence. For example, acquisition of the DWSE and DWSTE imaging signals can be interleaved within the same MRI acquisition pulse sequence. The imaging signals can comprise nuclear magnetic resonance (NMR) signals that can be processed to provide one or more images of the selected portion of the nervous system of the subject.

The plurality of sets of imaging signals comprise a first set of DWSE imaging signals associated with a first low-b- value that is at or near zero, a first set of DWSTE imaging signals associated with a second low-b-value that is at or near zero, and a second set of DWSTE signals that are associated with a high-b-value.

A signal difference between the DWSE imaging signals and the DWSTE imaging signals can be corrected based on the first set of DWSE imaging signals (associated with the first low-b-value that is at or near zero) and the first set of DWSTE imaging signals (associated with the second low-b-value that is at or near zero).

In various aspects, a high-b-value can be a b-value of at least or above 3,000 s/mm², at least or above 4,000 s/mm², at least or above 5,000 s/mm², at least or above 6,000 s/mm², at least or above 7,000 s/mm², at least or above 8,000 s/mm², at least or above 9,000 s/mm², at least or above 10,000 s/mm², or at least or above 12,000 s/mm². In exemplary aspects, each of the first and second low-b-values can be less than 100 s/mm². For example, optionally, the first low-b value can be from about 5 s/mm² to about 10 s/mm². Optionally, the second low-b-value can be from about 30 s/mm² to about 60 s/mm².

In various aspects, the plurality of imaging sets can comprise a plurality of sets of DWSE imaging signals and a plurality of sets of DWSTE imaging signals. For example, a plurality of sets of DWSE imaging signals can be provided with respective b-values from about 0 to about 1500 s/mm². Further, a plurality of sets of DWSTE imaging signals can be provided with respective b-values from about 0 to about 10,000 s/mm². The plurality of sets of DWSTE imaging signals can comprise a plurality sets of DWSTE imaging signals associated with respective high-b values.

In some optional aspect, each set of imaging signals can be provided in respective pixel maps. Each pixel map of the respective pixel maps can comprise a plurality of pixels associated with respective imaging signals at different spatial locations within the selected portion of the nervous system of the subject. Thus, each set of imaging signals can be used to produce a respective image having pixels associated with respective spatial locations. The pixels can be associated with respective imaging signals, such as, for example, intensity based on molecular diffusivity at each spatial location. Each pixel map can further be associated with a respective b-value and either DWSE imaging signals or DWSTE imaging signals.

Correcting the signal difference between the DWSE imaging signals and the DWSTE imaging signals can comprise calculating a pixel-by-pixel correction map comprising, for each pixel, a ratio of the imaging signal of the first set of DWSE imaging signals to the imaging signal of the first set of DWSTE imaging signals. At least one set of imaging signals can be multiplied by the pixel-by-pixel correction map.

In this way, one or more sets of DSWE imaging signals can be scaled to the one or more sets of DWSTE imaging signals, or, in the alternative, the one or more sets of DSWTE imaging signals can be scaled to the one or more sets of DWSE imaging signals. For example, the pixel-by-pixel correction map can comprise a matrix comprising ratio (at each pixel) of a DWSE imaging signal from the first set of DWSE imaging signals associated with the first low-b-value (e.g., b~0) to a DWSTE imaging signal from the second set of DWSTE imaging signals associated with the second low-b-value (e.g., b~0), and all sets of imaging signals associated with DWSTE can be multiplied by said pixel-by-pixel correction map to scale DWSTE to DWSE. In further optional aspects, aspects, the pixel-by-pixel correction map can comprise a matrix comprising, at each pixel, respective ratios of DWSTE imaging signals at b~0 to DWSE imaging signals at b~0, and all sets of imaging signals associated with DWSE can be multiplied by said pixel-by-pixel correction map to scale DWSE to DWSTE. In some optional aspects, the pixel-by-pixel correction map can comprise a respective ratio of DWSTE imaging signals at b~0 to DWSE imaging signals at b~0 (e.g., at each pixel). The DWSE signals can be multiplied by said pixel-by-pixel correction map to scale DWSE to DWSTE.

By correcting imaging signals as disclosed herein, a time correction is not required. Thus, a step of time correction (as is conventionally used to obtain high-b-value DWSTE imaging signals and is associated with a low signal to noise ratio) can be omitted. Accordingly, a fixed mixing time (TM) can be used. For example, the mixing time can be less than 500 ms, or less than 200 ms (e.g., about 100 ms). It is contemplated that a signal change by water exchange at a myelin sheath of a nerve bundle in ultra-high-b diffusion weighted imaging (UHb-DWI) can be more sensitive to TM, but increased TM induces a decrease in the number of images (as a function of an increased amount of time per image). Thus, time efficiency of measurement can be associated with a lower TM. Thus, TM can be fixed. In some aspects, TM can be fixed at less than 200 ms, or between 10 ms and 150 ms, or about 100 ms.

Optionally, the planar diffusion-weighted spin-echo (DWSE) imaging signals and planar diffusion-weighted stimulated-echo (DWSTE) imaging signals can be obtained with a reduced field of view. For example, the reduced field of view can comprise using two adiabatic full passage (AFP) pulses with a crusher gradient.

In some aspects, the selected portion of the nervous system of the subject comprises white matter of a spinal cord of the subject. In some aspects, myelination or axonal damage in the white-matter based on the planar imaging can be evaluated.

The diffusion-weighted imaging signals comprise radial diffusion-weighted imaging signals and/or axial diffusion-weighted images. It is contemplated that measuring both radial and axial DWI in one protocol can increase stability and time efficiency of the measurement from a human subject.

In some aspects, a system 100 can comprise a magnetic resonance imaging (MRI) system 102 that is configured to apply a diffusion-weighting gradient during acquisition of diffusion-weighted imaging signals from a selected portion of a nervous system of a subject. The MRI system can further be configured to obtain, simultaneously from the MRI system, planar diffusion-weighted spin-echo (DWSE) imaging signals and planar diffusion-weighted stimulated-echo (DWSTE) imaging signals to provide a plurality of sets of imaging signals. Accordingly, the system can be used to execute at least a portion of the methods disclosed herein.

The system 100 can further comprise a memory 1004 and at least one processor 1003 in communication with the memory. For example, the system 100 can comprise a computing device as further disclosed herein with reference to FIG. 9. The memory can comprise instructions that, when executed by the at least one processor, cause the processor to correct a signal difference between the DWSE imaging signals and the DWSTE imaging signals based on the first set of DWSE imaging signals and the first set of DWSTE imaging signals.

For example, the memory can comprise instructions that, when executed by the at least one processor, cause the processor to: calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

In various aspects, the high-b-value can be a value of at least or above 3,000 s/mm², at least or above 4,000 s/mm², at least or above 5,000 s/mm², at least or above 6,000 s/mm², at least or above 7,000 s/mm², at least or above 8,000 s/mm², at least or above 9,000 s/mm², at least or above 10,000 s/mm², or at least or above 12,000 s/mm². In exemplary aspects, each of the first and second low-b-values can be less than 100 s/mm². For example, optionally, the first low-b value can be from about 5 s/mm² to about 10 s/mm². Optionally, the second low-b-value can be from about 30 s/mm² to about 60 s/mm².

In some aspects, the magnetic resonance imaging system 102 can use a fixed mixing time. For example, in the some aspects, the mixing time can be less than 500 ms (e.g., about 100 ms).

In various aspects, the memory 1004 and at least one processor 1003 can be in communication with, or integral to, the MRI system 102. In further aspects, the memory and at least one processor can be in communication with the MRI system 102. In still further aspects, data from the MRI system 102 can be transferred subsequent to data collection (e.g., wirelessly, via wired connection, or via physically transferrable media such as a flash memory drive, etc.).

Thus, in some aspects, a computing device 1001 can comprise a memory 1004 and at least one processor 1003 in communication with the memory. The memory 1004 can comprise instructions that, when executed by the at least one processor, cause the processor to: receive simultaneously obtained planar diffusion-weighted spin-echo (DWSE) imaging signals and planar diffusion-weighted stimulated-echo (DWSTE) imaging signals that are provided as a plurality of sets of imaging signals. The plurality of sets of imaging signals can comprise a first set of DWSE imaging signals associated with a first low-b-value that is at or near zero, a first set of DWSTE imaging signals associated with a second low-b-value at or near zero, and a second set of DWSTE signals that are associated with a high-b-value.

The memory can further comprise instructions that, when executed by the at least one processor, cause the processor to correct a signal difference between the DWSE imaging signals and the DWSTE imaging signals based on the first set of DWSE imaging signals and the first set of DWSTE imaging signals. For example, the memory can comprise instructions that, when executed by the at least one processor, cause the processor to calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

In various aspects, the high-b-value can be a value of at least or above 3,000 s/mm², at least or above 4,000 s/mm², at least or above 5,000 s/mm², at least or above 6,000 s/mm², at least or above 7,000 s/mm², at least or above 8,000 s/mm², at least or above 9,000 s/mm², at least or above 10,000 s/mm², or at least or above 12,000 s/mm². In exemplary aspects, each of the first and second low-b-values can be less than 100 s/mm². For example, optionally, the first low-b value can be from about 5 s/mm² to about 10 s/mm². Optionally, the second low-b-value can be from about 30 s/mm² to about 60 s/mm².

Computing Device

Figure 9:
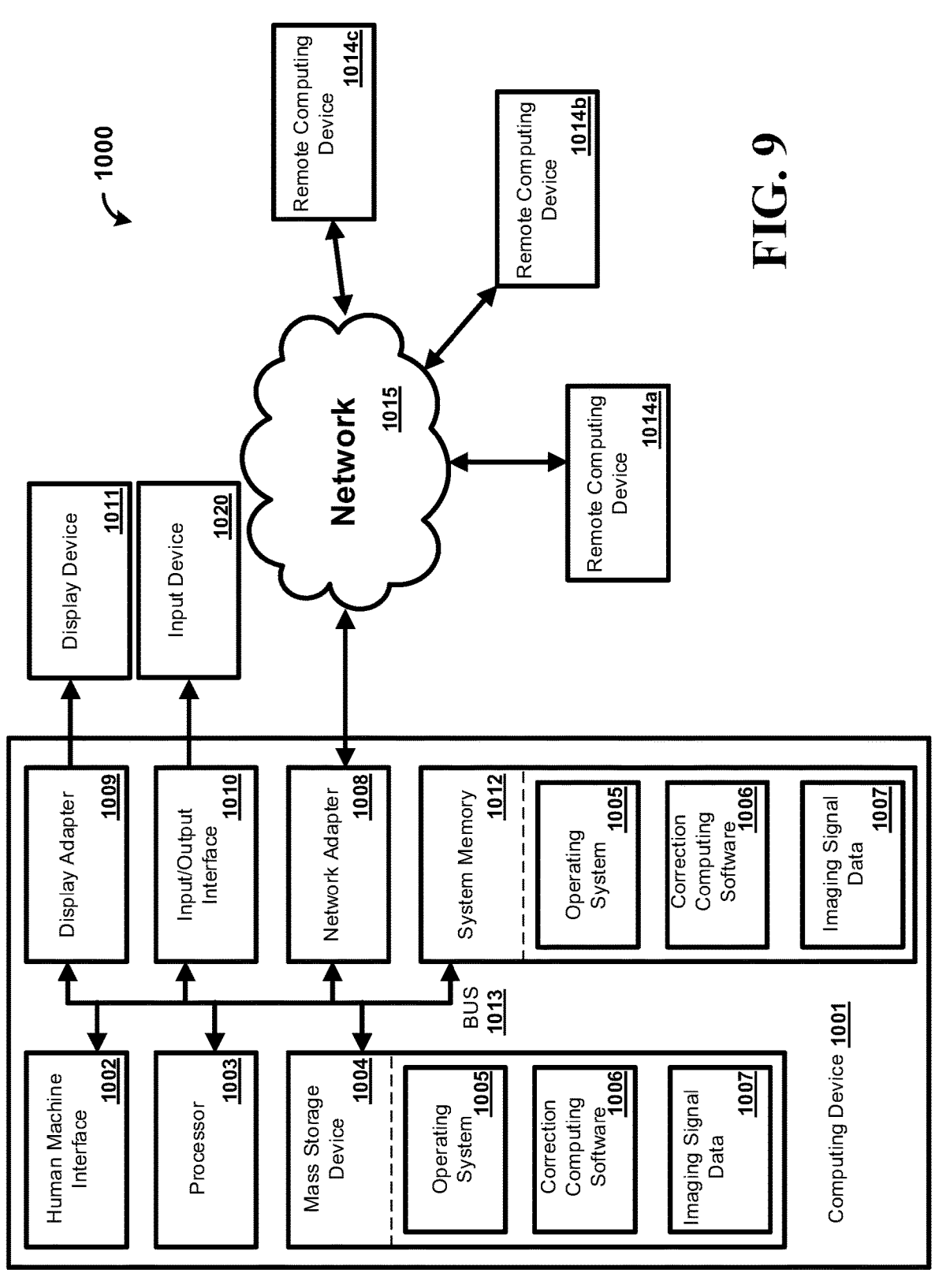
FIG. 9 illustrates an operating environment comprising a computing device as disclosed herein for use with the MRI system.

FIG. 9 shows an operating environment 1000 including an exemplary configuration of the computing device 1001. The computing device 1001 may comprise one or more processors 1003, a system memory 1012, and a bus 1013 that couples various components of the computing device 1001, including the one or more processors 1003, to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as imaging signal data 1007 and/or program modules such as operating system 1005 and (DWSE-DWSTE) correction computing software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EE-PROM), and the like.

Any number of program modules may be stored on the mass storage device 1004. An operating system 1005 and correction computing software 1006 may be stored on the mass storage device 1004. One or more of the operating system 1005 and orientation calculating software 1006 (or some combination thereof) may comprise program modules and the correction computing software 1006. Imaging signal data 1007 may also be stored on the mass storage device 1004. Imaging signal data 1007 may be stored in any of one or more databases known in the art. The databases may be centralized or distributed across multiple locations within the network 1015.

A user may enter commands and information into the computing device 1001 using an input device (not shown). Such input devices comprise, but are not limited to, a keyboard, pointing device (e.g., a computer mouse, remote control), a microphone, a joystick, a scanner, a touchscreen, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014*a,b,c*. A remote computing device 1014*a,b,c* may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014*a,b,c* may be made using a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014*a,b,c* can optionally have some or all of the components disclosed as being part of computing device 1001. In further optional aspects, the remote computing device 1014*b* can be a server that receives and stores logged data from the alignment device. In optional aspects, some or all data processing can be performed via cloud computing on a computing device or system that is remote to the computing device 1001.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of orientation calculating software 1006 may be stored on or sent across some form of computer readable media. Any of the disclosed methods may be performed by processor-executable instructions embodied on computer readable media.

Examples

Exemplary methods disclosed herein illustrate various aspects of the present disclosure. In one example, simultaneous measurement of a diffusion-weighted (DW) spin-echo and a DW stimulated echo signals in a single acquisition for ultra-high b DWI of cervical spinal cord were performed.

METHODS: DWSE and DWSTE images with b=0, which are measured by a simultaneous DWSESTE, differ by, (1) $T_1$ decay and diffusion weighting during the mixing time (time between the second and third RF pulses) for perfect 90° RF, and (2) imperfect 90° flipangles. The scale factor can be estimated by $S_{STE}(b=0)/S_{SE}(b=0)$ and multiplied to DWSE data. The combined data set is analyzed for UHb-DWI metric, such as low-b diffusion coefficient $D_L$ and high-b diffusion coefficient $D_H$, and for conventional diffusion tensor imaging (DTI) and diffusion kurtosis imaging (DKI) metrics including $\lambda_r$, $\lambda_a$, FA, and kurtosis K. A Monte-Carlo Simulation was performed for water diffusion within a 1D nerve fiber to investigate how two different diffusion times, i.e., short $\Delta_L$ for low-b DWSE and long $\Delta_H$ for high-b DWSTE, on the combined data set.

RESULTS: Sets of low-b DWSE and high-b DWSTE images, including b=~0 s/mm², were measured within a single acquisition, and the correction map was calculated by dividing DWSTE (b=0) by DWSE (b=0), and multiplied to all DWSE images in pixel-by-pixel. The combined DWSESTE data provided ADC value of D=2.052×10⁻³ mm²/s for bulk water at room temperature (20° C.). DWSESTE was applied to a healthy human CSC. ROI was selected on the ventrolateral motor white-matter, and the radial DWI data set was fit to a double-exponential function, resulting ($D_L$, $D_H$)=(0.894, 0.063)×10⁻³ mm²/s. The axial DWI data fit well to a single-exponential function with diffusivity 2.66× 10⁻³ mm²/s. The apparent diffusion coefficient and kurtosis were also estimated by fitting rDWI and aDWI data with b=0~2500 s/mm² as $ADC_r$ ($=\lambda_r$)=0.504×10⁻³ mm²/s and $K_r$=1.857 for radial DWI and $ADC_a$ ($=\lambda_a$)=2.503×10⁻³ mm²/s and $K_a$=0.755 for axial DWI, respectively. The resultant fractional anisotropy FA is 0.768. Monte-Carlo Simulation indicated a negligible difference between a DWSE with short $\Delta_L$ and DWSTE with a long $\Delta_H$ at b<1500 s/mm².

CONCLUSIONS: DW spin-echo and stimulated-echo images are successfully measured in a single acquisition pulse sequence in a half the imaging time compared with the conventional DWSTE technique, and combined for ultra-high-b DWI of human CSC imaging. The combined data set provides a reliable signal-b curves for further quantitative analysis of UHb-DWI method. The combined data can also be used to estimate the conventional DTI and DKI metrics.

| List of Abbreviations | |
| --- | --- |
| abbreviation | Full words |
| 2D ss-DWSESTE | 2D singleshot Diffusion-Weighted Spin-Echo and STimulated-Echo |
| ADC | Apparent Diffusion Coefficient |
| CSC | Cervical Spinal Cord |
| DIR | Double Inversion Recovery |
| DKI | Diffusion Kurtosis Imaging |
| DTI | Diffusion Tensor Imaging |
| DWSE | Diffusion-Weighted Spin-Echo |
| DWSTE | Diffusion-Weighted STimulated-Echo |
| DWSESTE | Diffusion-Weighted Spin-Echo and STimulated-Echo |
| EPI | Echo-Planar Imaging |
| IMIV | Interleaved Multi-Inner-Volume |
| MCS | Monte-Carlo Simulation |
| MPI | Message Passage Interface |
| rFOV | reduced Field-Of-View |
| SESTEPI | Spin-Echo and STimulated-Echo EPI |
| SNR | Signal-to-Noise Ratio |
| UHb-DWI | Ultrahigh-b DWI |
| UHb-aDWI | Ultrahigh-b axial DWI |
| UHb-rDWI | Ultrahigh-b radial DWI |

Methods and Materials

The development and experiment of 2D ss-DWSESTE were performed on a clinical whole-body MRI system, which is equipped with maximum gradient 80 mT/m and 200 mT/m/s slew-rate, using IDFEA, a pulse-sequence development environment software (Siemens Medical Solution, Erlangen, Germany). For current work, Stejskal-Tanner diffusion scheme was utilized.

Pulse Sequence: Manufacturer's, i.e. Siemens', 2D singleshot diffusion-weighted EPI sequence was modified to implement 2D singleshot DW-SESTE, as illustrated in FIG. 1, using a pulse sequence development environment (IDEA, Siemens Medical Solution, Erlangen, Germany). In brief, the flipangle of the refocusing RF was changed to 90° from 180°, and the plugin event groups for {90°–$G_D$} and {EPI-ReadOut} are replayed at the mixing time TM after the beginning of the second 90° pulse. Then, delay after the all events is reduced accordingly. The reduced FOV (rFOV) was achieved either using manufacturer's 2D RF pulse or double-inversion-recovery (DIR) pulses with appropriate crusher[14,15] and diffusion-filter gradients[16], which are enclosed within the red dotted box in FIG. 1. Diffusion filter can be used to suppress bulk water signal, such as in cerebrospinal fluid (CSF) and edema, before applying $G_D$ parallel to the nerve fiber, i.e., axial DWI[6]. The echotime TE of the DWSTE becomes identical to that of the DWSE. Three diffusion gradients are applied with the identical duration and amplitude, and with separation $\Delta_L$ and $\Delta_H$ for DWSE and DWSTE, respectively. Diffusion-weightings for the low-b DWSE and high-b DWSTE are $b_L=(\gamma G_D\delta)^2(\Delta_L-\delta/3)$ and $b_H=(\gamma G_D\delta)^2(\Delta_H-\delta/3)$, respectively.

Combining DWSE and DWSTE: Due to the RF inhomogeneity, the actual flipangle at position r within the imaging field-of-view (FOV) is not 90°, rather $\alpha(\vec{r})$. Then, the equations for DWSE and DWSTE signal intensities are derived as[13], $$M_{SE}(\vec{r}; b_L) = M_+^\circ(\vec{r})\sin\alpha \cdot \sin^2\alpha/2 \cdot e^{-TE/T_2} \cdot e^{-bD_L} \quad (1)$$

$$M_{STE}(\vec{r}; b_H) = 0.5\ M_+^o(\vec{r})\sin^3\alpha \cdot e^{-TM/T_1} \cdot e^{-TE/T_2} \cdot e^{-bD_H} \quad (2)$$

These formulas become $$M_{SE}(\vec{r}; b_L) = 0.5\ M_+^o(\vec{r})\ e^{-TE/T_2} \text{ and}$$

$$M_{STE}(\vec{r}; b_H) = 0.5\ M_+^o(\vec{r})e^{-TM/T_1}e^{-TE/T_2}$$

for a set of perfect 90° for all three RF pulses. However, in reality particularly in MR imaging, the actual flipangle at specific position $\vec{r}$ deviates from 90°. Therefore, DWSE and DWSTE signals differ by, (2) imperfect 90° RF pulses, and (b) additional $T_1$ decay on the restored longitudinal magnetization. Therefore, low-b DWSE images can be combined to DWSTE data by multiplying a position-dependent correction map g ($\vec{r}$; $\alpha$, $T_1$) as in, $$M_{STE}(\vec{r};b_L)=M_{SE}(\vec{r};b_L)\cdot g(\vec{r};\alpha,T_1) \quad (3)$$

Here, the correction map g($\vec{r}$; $\alpha$, $T_1$) can be estimated using DWSE and DWSTE images with b=0, $$g(\vec{r}; \alpha, T_1) = 2\cos^2\frac{\alpha}{2} \cdot e^{-TM/T_1} = \frac{M_{STE}(\vec{r}; 0)}{M_{SE}(\vec{r}; 0)} \quad (4)$$

Eq. (4) indicates that the DWSTE signal intensity increases and DWSE signal intensity decreases with the tipup RF pulse with the flipangle smaller than 90°. There is no need to measure the actual, position-dependent flipangle $\alpha(\vec{r})$. Any difference between DWSE and DWSTE with a TM is directly related to this correction function. Therefore, the correction function g($\vec{r}$; $\alpha$, $T_1$) can be estimated by dividing DWSTE (b=0) image by DWSE (b=0) image.

MR Imaging: 2D ss-DW-SESTEPI was applied to a fluid phantom, filled with 0.1 mMol $MnCl_2$/water, of which $T_1$ and $T_2$ of water proton were previously estimated as 950 ms and 80 ms, 1×1 mm$^2$ in-plane resolution and 4 mm slice thickness, TR 4900 ms for 21 slices, TE 76 ms, 8 signal averaging, DWSE and DWSTE images with ($b_L$, $b_H$) values (0, 0) and 7 pairs of ((40, 264), (80, 528), (130, 858), (170, 1123), (210, 1387), (250, 1651)) s/mm$^2$ and ((20, 132), (40, 264), (80, 528)) s/mm$^2$ along two orthogonal directions.

This approach was then applied to CSC of a healthy subject to obtain a set of UHb-DW images using the manufacturer's 64 channel head/neck array coil, under an approved IRB, using the identical imaging parameters as those for phantom, except for 7 pairs of DWSE and DWSTE with b values ((250, 1620), (500, 3240), (750, 4860), (1000, 6480), (1250, 8100), (1500, 9720)) s/mm$^2$ and ((130, 842), (250, 1620), (500, 3240)) s/mm$^2$ along perpendicular (radial) and parallel (axial) to the cord direction, respectively. For correction, additional set of DWSE and DWSTE were measured with ($b_L$, $b_H$)=(0, 0), common for rDWI and aDWI. The duration $\delta$ and separations for low-b and high-b ($\Delta_L$, $\Delta_H$) DWI are 18.5 ms, 22.4 ms, and 123 ms, respectively. The phase-FOV was set to 25% as is for cervical spinal cord imaging in transaxial plane. To remove the aliasing artifact caused by the signal outside the phase-FOV, a 2D excitation RF was used, which is termed as "ZoomIt" in Siemens platform. The pulse sequence is capable of reading a text table and listing a set of diffusion-encodings with the direction and amplitude of diffusion gradient. Data acquisition time for UHb-DWI was about 6 min for twenty-one slices covering C1~T2 vertebras. The measured DWIs are processed, including selecting ROIs and analyzing signal-b curves, at an offline UNIX computer using a home-developed software, which is programmed in Python 3.x with pydicom (https://github.com/pydicom/pydicom) for reading DICOM data.

For DKI analysis, entire combined DWI data of each ROI were first fit to a biexponential function, then, the fitted data with b≤2500 s/mm$^2$ were fit to the diffusion kurtosis formula $S(b)=S_o e^{-bD}\ e^{K(bD)2/6}$ to estimate the conventional DTI/DKI metrics of D, fractional anisotropy (FA), and kurtosis K[17,18]. Here, the decay constant D in the signal-b curve of rDWI and aDWI can be considered as the apparent diffusion coefficients $ADC_r$ and $ADC_a$ along radial and axial direction in conventional DWI/DWI, respectively, and used to calculate the $$FA = (ADC_a - ADC_r)/\sqrt{ADC_a^2 + 2ADC_r^2},$$

assuming a cylindrically symmetric local system, i.e., $ADC_r=\lambda_2=\lambda_3$.

To compare the performances of reduced-FOV using between 2D RF excitation and double-inversion-recovery (DIR) method, an additional MRI experiment was conducted on a fluid phantom. Imaging parameters, particularly the width of the diffusion gradient pulse, were adjusted to maintain the ratio $b_{STE}/b_{SE}=6.0$.

Figures 2A, 2B:
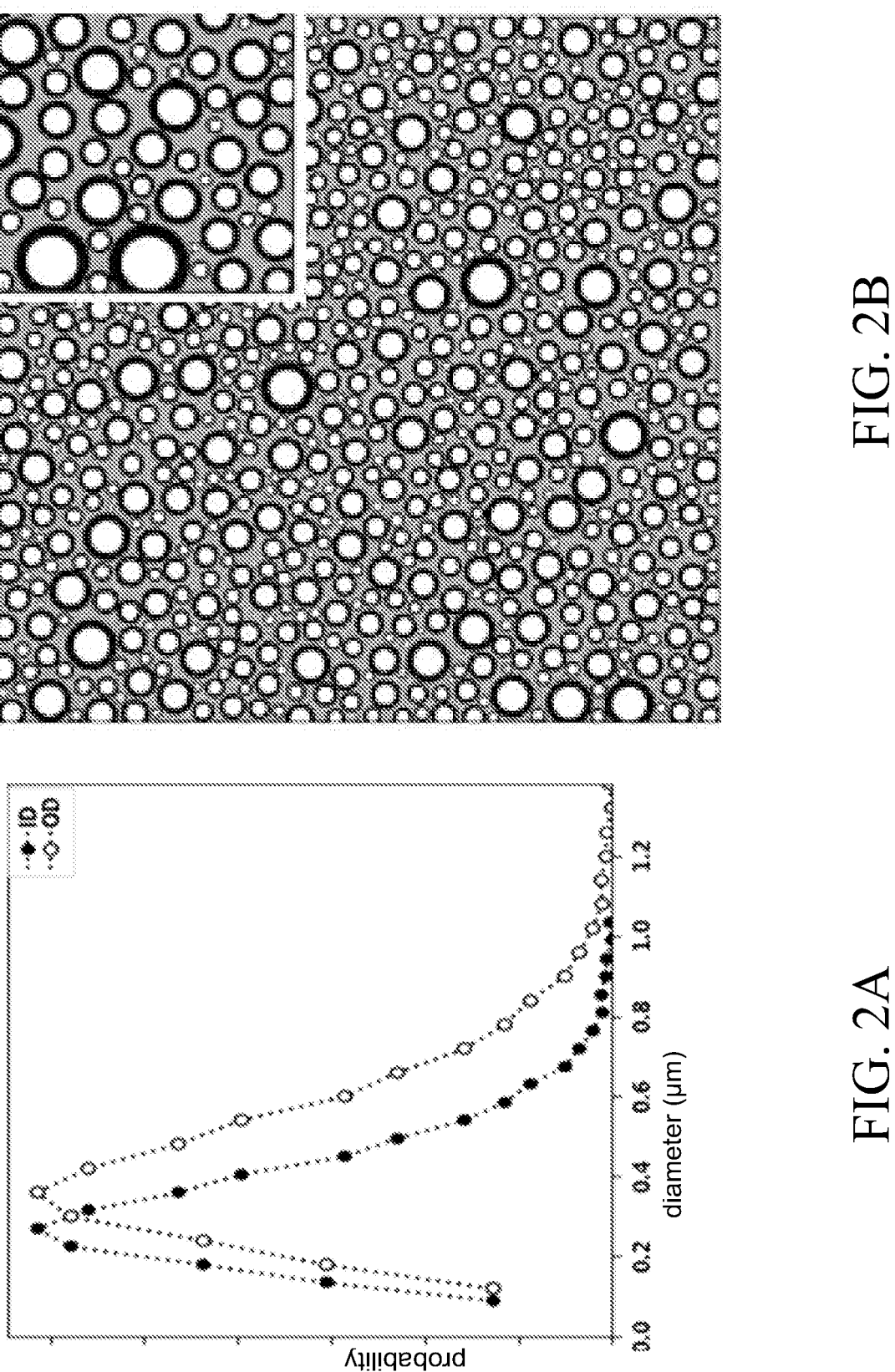
FIG. 2A is a plot showing a Monte Carlo simulation (MCS).
FIGS. 2B-D illustrate cross-sectional images of synthetic spinal cord using (a) axonal size distribution with a γ-variate function peaked at 0.38 am, and positions of 20,000 water molecules at (c) t=0 and (d) 106 ms. (c) indicates the cross-sectional image of the white-matter geometry with a loss of 25% axons. The closed and open circles in FIG. 2A represent, respectively, sizes of inner (i.e. IA) and outer diameters, including myelin sheath, of the axons. The gray colored dots in FIGS. 2C-2D indicate water molecules in EA space, which is illustrated more clearly in the inserted pictures.
Figure 2D:
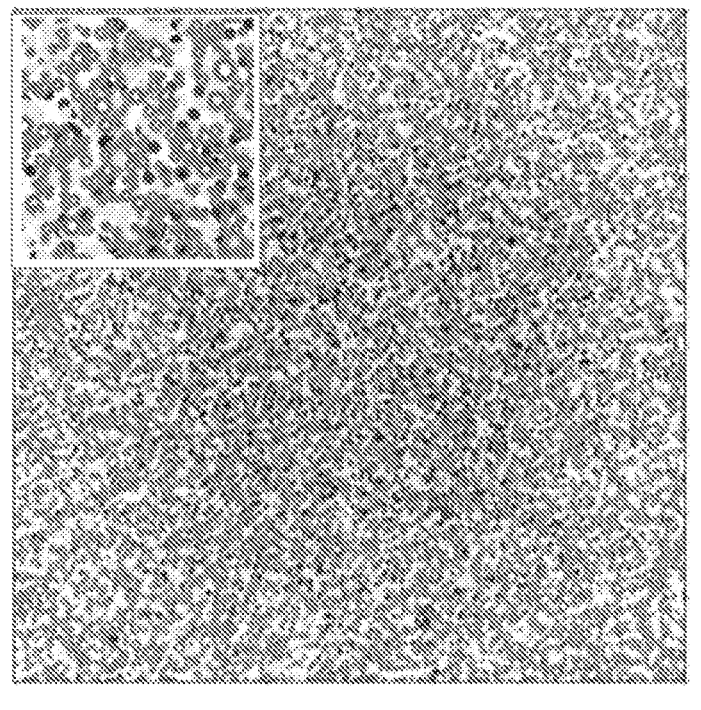
Figure 2C:
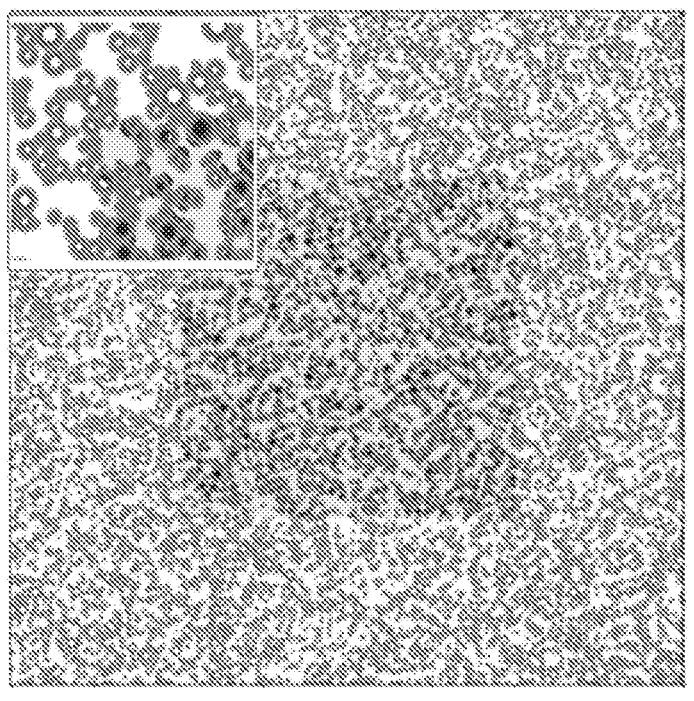

Monte-Carlo Simulation (MCS) of water diffusion within white-matter: Numerical MCS experiment was performed for water diffusion within one dimensional spinal cord in order to investigate the effect of diffusion time on DWSE and DWSTE, using home-developed MCS software[4] with Python and MPI (Message Passage Interface) C++. The step-by-step procedure for MCS is described in detail in Jeong, K. E.; Lee, S. Y. J.; Yeom, S. K.; Carlson, N. G.; Shah, L. M.; Rose, J. W.; Jeong, E. K. Ultrahigh-b DWI (UHb-DWI) for Quantitative Evaluation of Myelination in Shiverer Mouse Spinal Cord. *Magn Reson Med* 2021, in-print, PMID: 34418157 DOI: 10.1002/mrm.28978. https://doi.org/10.1002/mrm.28978[19], which is hereby incorporated by reference herein in its entirety. MCS was performed for 3200 circular axons with g-ratio of 0.67 on an 80×80 μm² 2D pixel as illustrated in FIG. 2*b*, on where 20,000 water molecules are randomly distributed at time zero at the central 25% as illustrated in FIG. 2*c*. The size of the myelinated axons is determined by a γ-variate size distribution function with 1.2 μm peak diameter ($\overline{d}_{pk}$)[20], as shown in FIG. 2*a*. The relative occupations of intra-axonal (IA) space, myelin space, and extra-axonal (EA) space are 0.30, 0.39, and 0.31, respectively. Note that cellular space includes both IAS and myelin space, therefore, 69%. The 2D imaging pixel is divided to 2500×2500 grids, of which grid resolution is 32 nm. The pre-processed data also include if a specific grid point belongs to IA or myelin space of the nth axon, or EA space. During the actual MCS processing, water molecules are allowed to make a random hopping every 0.1 μs ($\Delta t_{hop}$) and their positions are recorded every 10 μs ($\Delta t_{sav}$) for a set of simulation parameters, including total diffusion time of 150 ms and permeabilities $P_{H_2O}$=0.0, 7.0, and 100 μm/s. For each microscopic hopping, i.e., in every $\Delta t_{hop}$, diffusion coefficient of the pure water at 37° C. was assigned as 3.0×10⁻³ mm²/sec, which is the typical measured value at in-vivo brain CSF[21].

Results

Figures 3A, 3B, 3C, 3D:
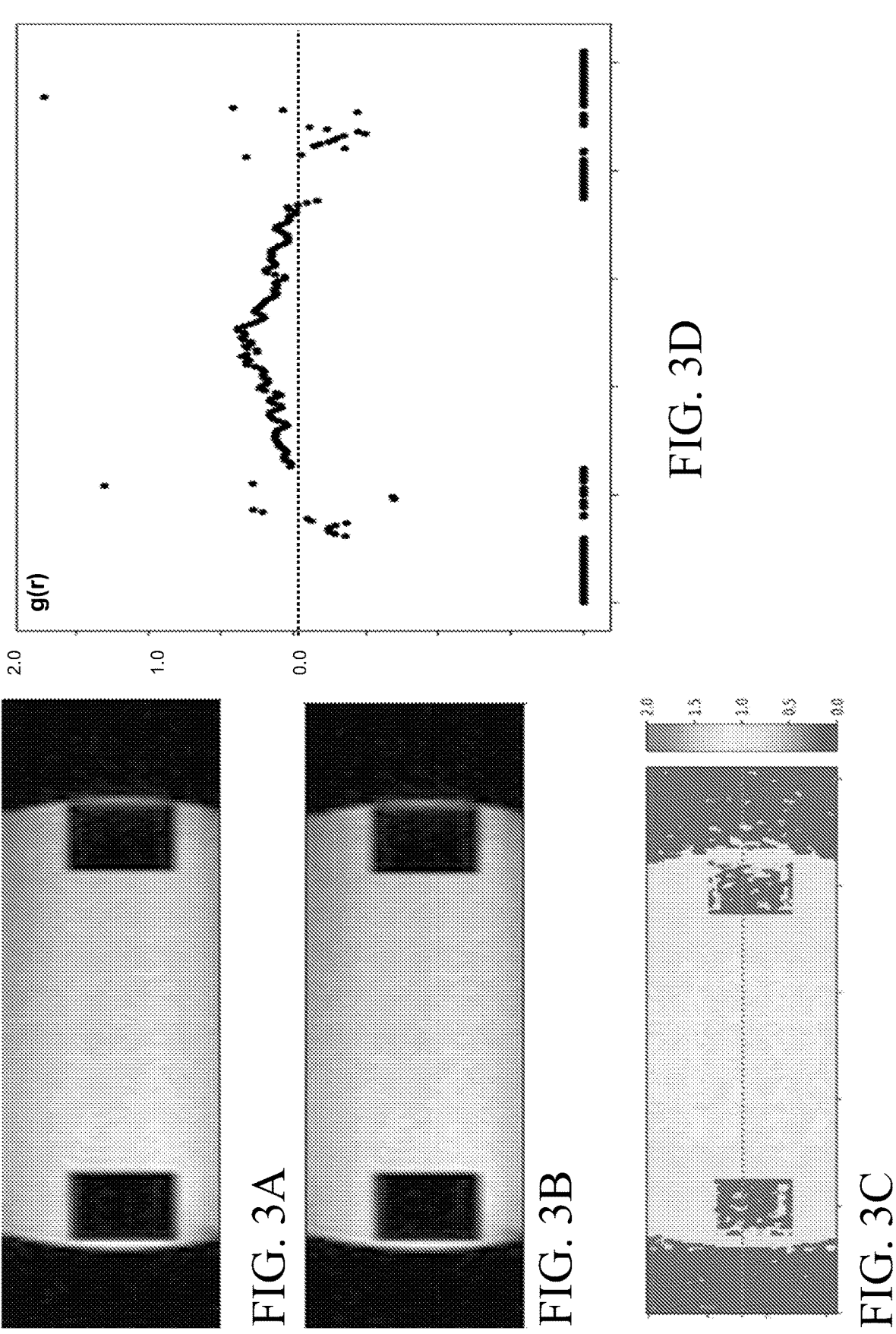
FIGS. 3A and 3B are plots of, respectively, Raw DWSE and DWSTE images.
FIG. 3C is the resultant g(r) map of a center slice. The correction map $g(\vec{r})$ was constructed by simply dividing DWSTE by DWSE in pixel-by-pixel. The correction values $g(\vec{r})$ in the central region in FIG. 3C are slightly larger than 1.0, as the profile plot in FIG. 3D indicates along a horizontal dotted line in FIG. 3C.

FIGS. 3A-C illustrate raw DWSE and DWSTE images and the corresponding correction map $g(\vec{r})$ of a center slice, respectively. Because the body-coil was used for RF transmission, the actual flipangles of the applied RF pulses are expected to be very close to 90°. However, the calculated correction map g(r) in FIG. 3C indicates g(r) value larger than 1.0 at the central portion (yellowish). Based on eq. (4), g(r) values above the g(r)=1 line in FIG. 2*d* is caused by the flipangle α slightly smaller than 90°. Even for the image pixels with α=90°, g(r) is supposed to be smaller than 1.0 by $e^{-TM/T_1}$ (=0.1 for TM/T₁=0.1 s/0.95 s). As indicated by eq. (4), correction is as straightforward as dividing the DWSTE (b=0) image by DWSE (b=0) image and multiplying to every DWSE image.

Figures 4A, 4B:
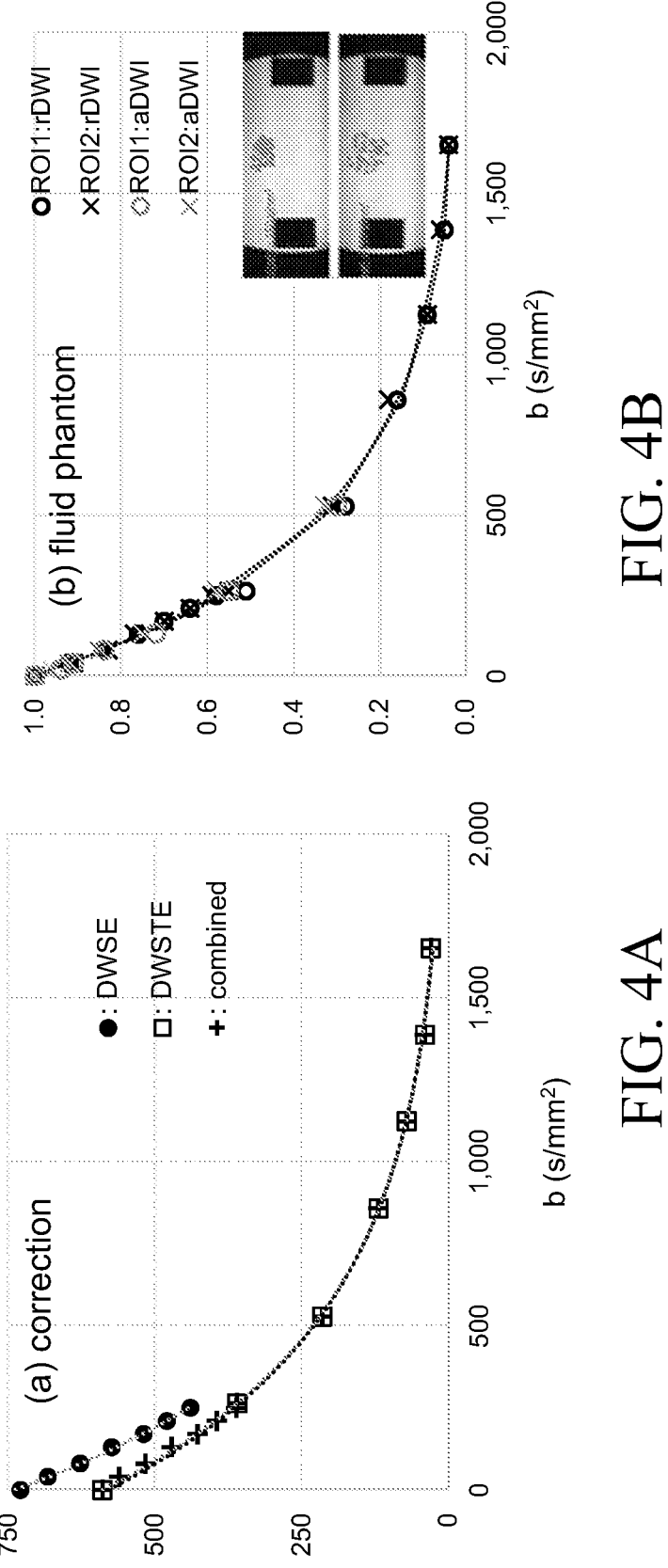
FIG. 4A illustrates a plot of Raw DWSE (●) and DWSTE ( ), and combined data (+)
FIG. 4B illustrates a plot of signal-b curves of two separate ROIs on DW images with two diffusion directions (rDWI and aDWI). Signal-b curves fit well to a single-exponential function for the phantom data in FIG. 4B.

FIG. 4A displays raw data of DWSE (●) and DWSTE ( ), and combined data (+) for a selected ROI on the phantom DWSESTE images. The raw DWSTE signals are about 20% lower than the raw DWSE signals, which is likely caused by a smaller than 90°. These DWSE data are multiplied by the correction factor $g(\vec{r})=S_{STE}(\vec{r}; b=0)/S_{SE}(\vec{r}; b=0)$ in pixel-by-pixel, and then added to DWSTE data set, as plotted as (+) symbol. Because the water diffusion is isotropic, i.e., no orientation dependent, for a uniform fluid phantom, the signal-b curves of DWI along two perpendicular directions should be identical, as plotted as black and red symbols in FIG. 4B for selected pixels on insert images. The signal-b curves of aDWI and rDWI data for two separate ROIs in FIG. 4B demonstrate how well the correction algorithm works. From the combined image set, diffusion coefficient of the water at room temperature is estimated as D=2.052×10⁻³ mm²/s, which is close to reported value at room temperature[22,23].

Figure 5:
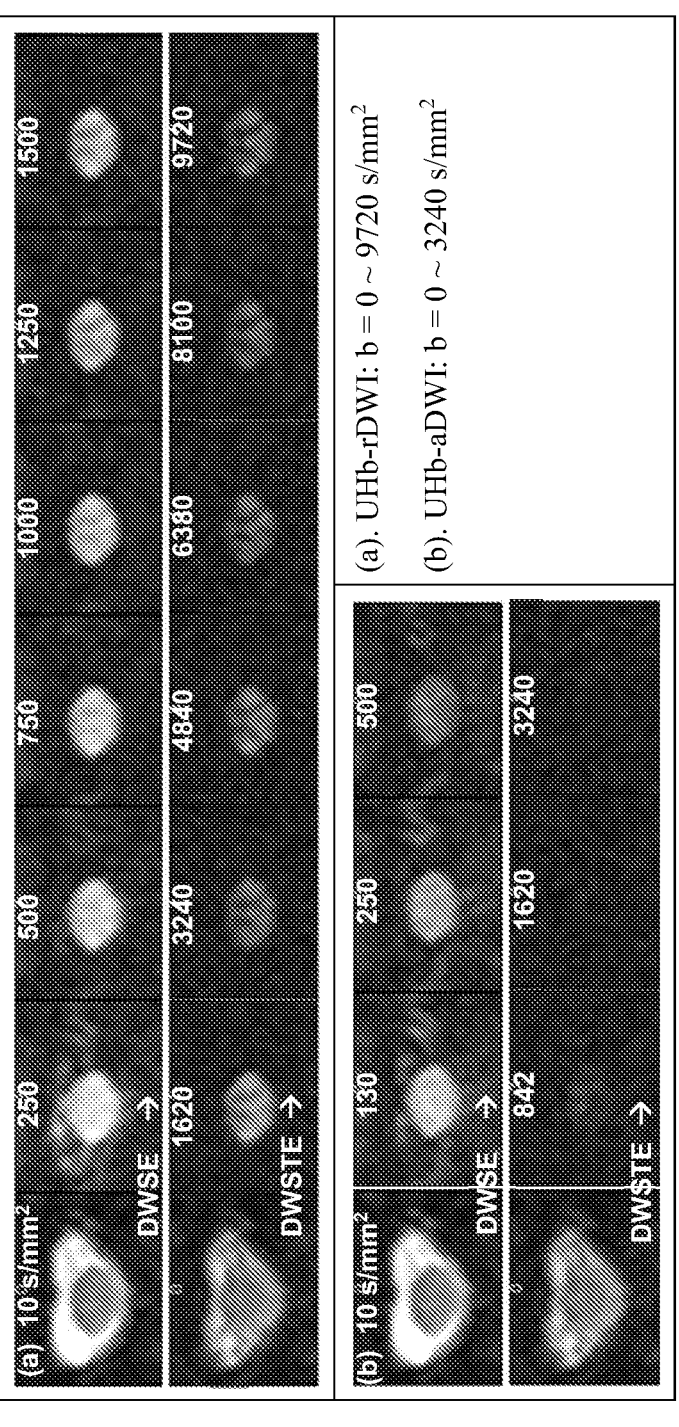
FIG. 5 shows UHb-rDWI images of cervical spinal cord at the level C3/C4: (a). UHb-rDWI with b=0~9720 s/mm² and (b). UHb-aDWI with b=0~3240 s/mm², measured using 2D ss-DWSESTE from a healthy subject. Note that even at b=9720 s/mm² rDWI, there is still large signal left on the white-matter tracts, where the water movement is restricted perpendicular to the fiber direction. In aDWI, white-matter signal is suppressed to noise level at b=842 s/mm², while that of gray-matter signal is visible.

All UHb-rDWI images of the center slice from a healthy subject's CSC are illustrated in FIG. 5. Images in top row of FIG. 5 at (a) are DWSE images with b=250~1500 s/mm², which were corrected for imperfect 90° and T₁ decay effects, and those in bottom row are DWSTE with b=1620~9720 s/mm². B values of DWSTE are amplified by 6.48 times (=($\Delta_H$-δ/3)/($\Delta_L$-δ/3)). UHb-aDWI images are illustrated in FIG. 5 at (b). In healthy white-matter, the signal at high-b DWI, such as b>5,000 s/mm², is mainly due to the intra-axonal water or motion that is only parallel to the axonal fibers, except at the Node of Ranvier where axonal membrane is directly exposed to the extra-cellular space.

Figures 6A, 6B, 6C, 6D:
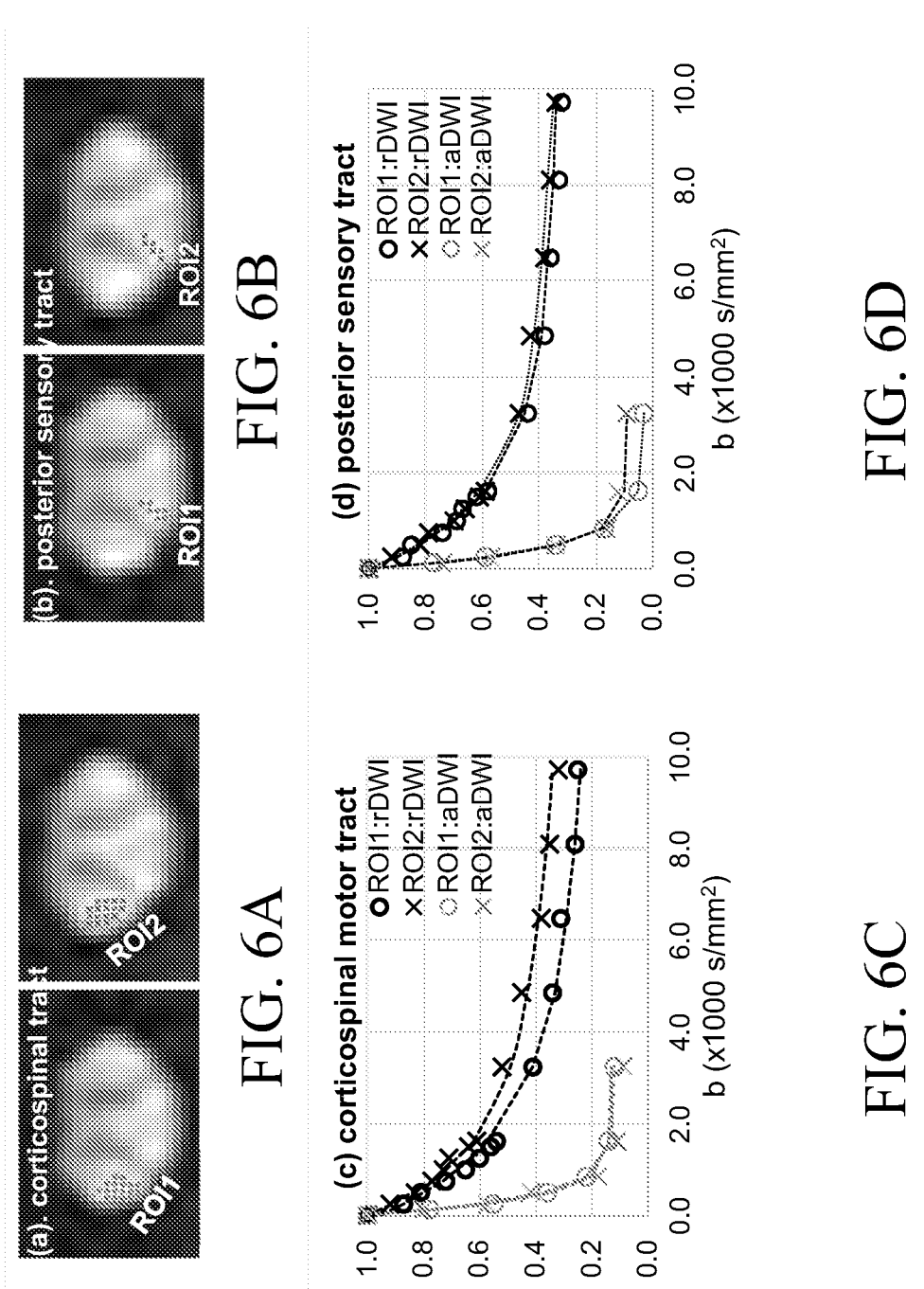
FIGS. 6A and 6B show, respectively ROIs
FIGS. 6C and 6D show signal intensity vs. b curves on (FIG. 6A, 6C) corticospinal motor tract and (FIG. 6B, 6D) posterior sensory tract at two slices (C3-C4 and C2-C3) separated by 15 mm, with UHb-rDWI (O, X) (above UHb-aDWI) and UHb-aDWI (O, X) (below UHb-rDWI). Signal-b curves fit well to a single exponential function for UHb-aDWI (O, X), and a double-exponential function for UHb-rDWI data (O, X) in (b, d). Note that the maximum b-values for UHb-rDWI (O, X) and UHb-aDWI (O, X) are 9720 and 3420 s/mm², respectively.

Two DWI images of a healthy CSC, separated by 15 mm, are shown in FIG. 6A. Signal intensities of two ROIs at corticospinal tracts are plotted with respect to b values in FIG. 6B. The axial-DWI signal (red symbols in FIG. 6B) of multi-pixel ROIs in FIG. 6A fit well to a single-exponential function with respect to b value with diffusivity 2.66×10⁻³ mm²/s. However, human radial-DWI (rDWI) signal fits to a double exponential function. The decay constants of the fast and slow components were ($D_L$, $D_H$)=(0.894, 0.063)×10⁻³ mm²/s with relative fractions (54%, 46%) at the corticospinal tract and (0.675, 0.020)×10⁻³ mm²/s with relative fractions (56%, 44%) at the dorsal sensory tract, respectively. These values are within the ranges of previously reported values, which were measured using variable diffusion time at MRI system with half the gradient strength[5,6]. The mean $D_H$ values of healthy controls at lateral corticospinal and posterior sensory tracts at the C3-C4 level were reported as (0.0505±0.0306)×10⁻³ and (0.0312±0.0205)×10⁻³ mm²/s, respectively[6]. The apparent diffusion coefficient and kurtosis were estimated by fitting rDWI and aDWI data with $b_{max}$=2500 s/mm² as ($ADC_r$, $ADC_a$)=(0.504, 2.503)×10⁻³ mm²/s with ($K_r$, $K_a$)=(1.857, 0.755) for the lateral corticospinal tract and ($ADC_r$, $ADC_a$)=(0.401, 2.681)×10⁻³ mm²/s with ($K_r$, $K_a$)=(1.920, 0.525) for the posterior column, respectively. The resultant fractional anisotropy FA is 0.768 and 0.832, respectively. Note that the diffusion coefficient of the in-vivo brain CSF water, i.e., at 36.5° C., was around 3.0×10⁻³ mm²/s[21].

Figure 7C:
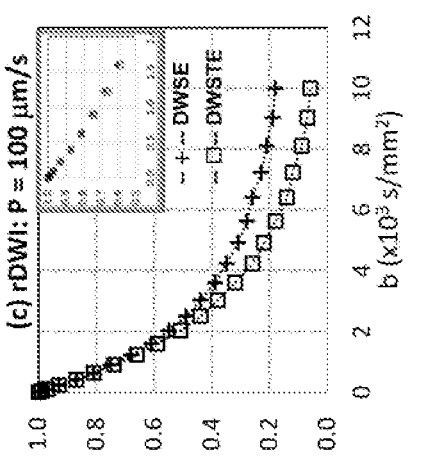
FIGS. 7A-F illustrate normalized signal-b curves of permeability (FIGS. 7A,7D) 0 μm/s, (FIGS. 7B,7E) 7 μm/s, and (FIGS. 7C,7F) 100 μm/s for (*, X, +) DWSE with $\Delta_L$=22.4 ms and ( ◇, O, □) DWSTE with $\Delta_H$=123 ms. Plots (a~c) and (d~f) represents rDWI and aDWI data, respectively. Note that the signal-b curve for permeability 0.0 μm/s, i.e., no exchange at the myelin sheath, has two components; fast decaying component at low-b region from EA water and plateau at high-b region from IA water. Insert figures are DWI signals replotted with b<2000 s/mm², where DWSE images are measured in a human CSC protocol. For DWI along axial direction, i.e., aDWI, signal-b curve for both DWSE and DWSTE are almost identical, because there is no restriction along the axonal tubule direction.
Figure 7F:
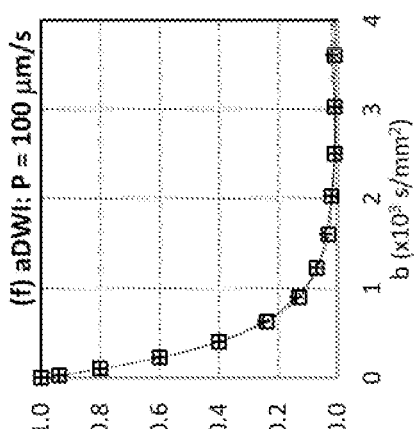
Figure 7B:
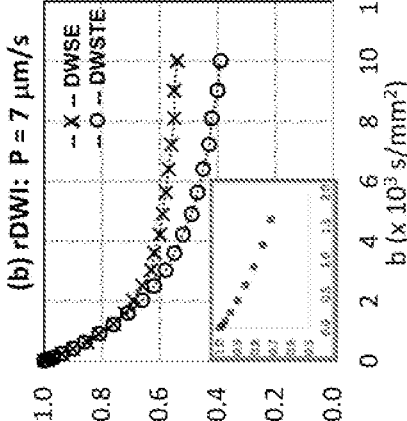
Figure 7E:
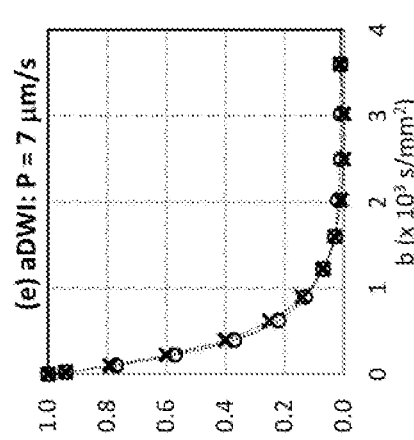
Figure 7A:
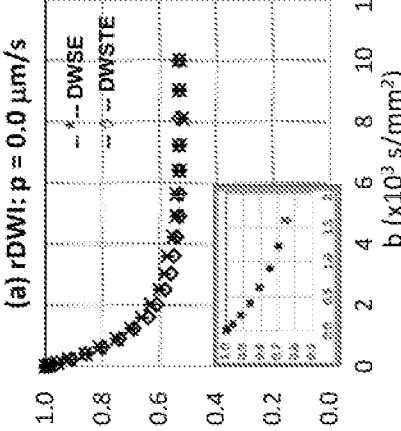
Figure 7D:
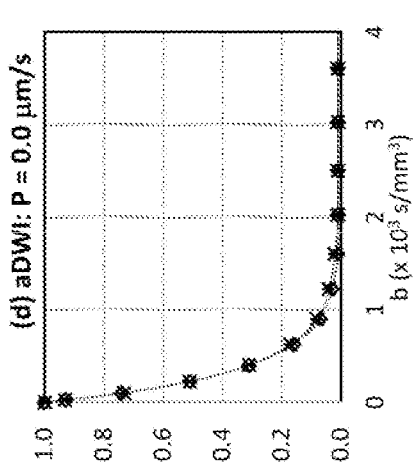
Figure 8:
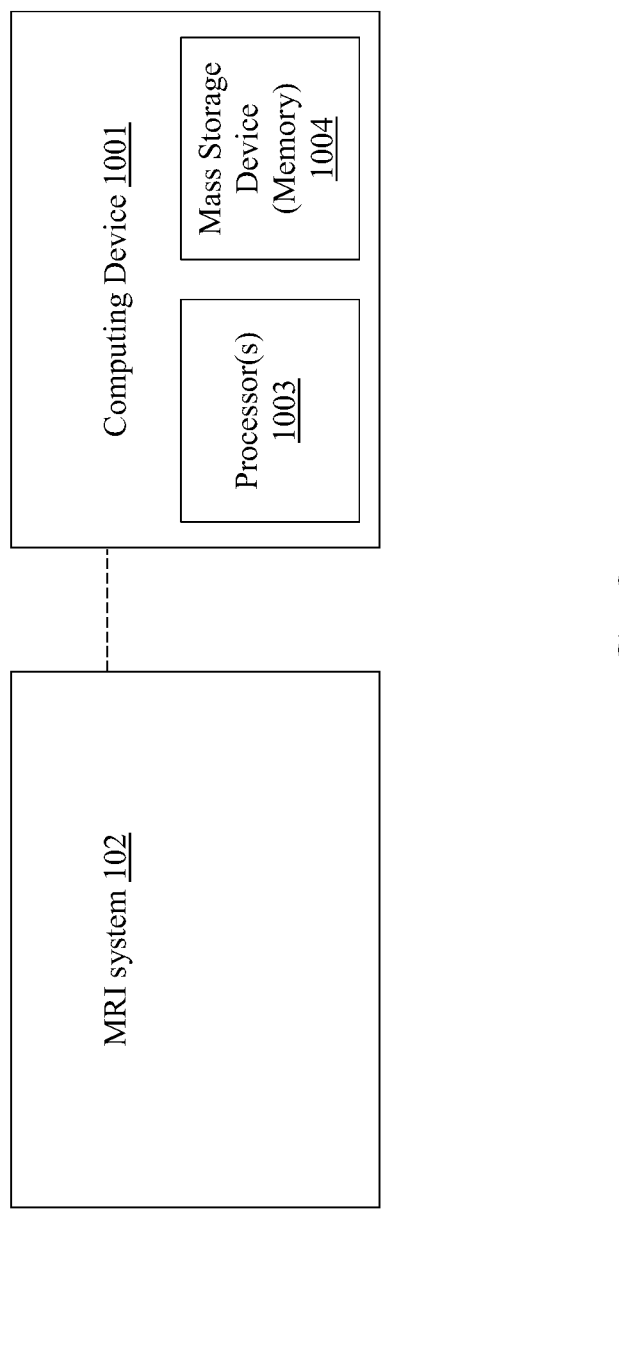
FIG. 8 illustrates an exemplary system as disclosed herein.

FIGS. 7A-F illustrates the synthetic signal-b curves of DWSE and DWSTE signals, which are numerically generated for three water permeabilities of $P_{H_2O}$=0.0, 7.0, and 100 μm/s, using MCS data and eq. (9) with δ=18.4 ms, $\Delta_L$=22.4 ms, and $\Delta_H$=123 ms, the same duration and separation for the experimental UHb-rDWI. The signal-b curves of DWSE and DWSTE for $P_{H_2O}$=0.0 μm/s slightly differ at low-b region, where EA water molecules diffuse through. If EA space is completely open, as in pure bulk water, these two signal-b curves must be identical, as indicated by FIGS. 7D-F for aDWI signal-b curves. For non-zero permeability at the myelin sheath, at a specific diffusion-weighting b-factor, DWI signal decays more with DWSTE with larger diffusion time than that of DWSE with small diffusion time. However, at low-b region below b<2,000 s/mm², where extra-cellular water signal dominates the change in DWI, difference between DWSE and DWSTE curves is negligible for all three permeabilities. In fact, the difference is slightly larger with larger permeability as in FIG. 7C, as the insert plot indicates, compared with that in FIG. 7A and FIG. 7B. These MCS results indicate that the error in combining DWSE and DWSTE signal is minimal.

Discussion

To reduce the geometric distortion in EPI-based imaging, rFOV has been applied using outer-volume suppression (OVS)[24], 2-dimensional excitation RF pulse[25], or double-inversion recovery (DIR) pulses[14,15] rFOV using OVS is a simple but its performance heavily depends on the performance of suppression RF pulse. Although the performance of rFOV using 2D RF or DIR was not compared, the duration of the 2D RF pulse tends to be long in MRI system with a single transmit channel, thus, it may be available only in MRI system with multi-channel transmits. To reduce the transition-band width, oversampling id typically used along the phase-encoding direction, which further increases the distortion. rFOV using DIR can be applied on any MRI system with or without multichannel transmit capability. The edge in the PE direction was sharp by using adiabatic inversion pulses. A major disadvantage of rFOV using DIR is that the longitudinal magnetization of a specific imaging slice is decreased by frequent applications of double inversion RF pulses for other slices. The reduction in the measured signal was inversely proportional to the number of interleaving slices[15].

The most important advantage of 2D ss-DWSESTE is that the use of full magnetization for UHb-DWI measurement compared with the conventional DWSTE technique. A low-b DWSE and a high-b DWSTE are measured within the single acquisition. It involves a correction processing to remove the effect of un-even distribution of diffusion-prepared magnetization between DWSE and DWSTE images, which is caused by imperfect 90° in the stimulated-echo pulse sequence and further signal decay by $T_1$ in DWSTE. The correction processing includes, (1) constructing correction map $g(\vec{r})$ by dividing DWSTE(b=0) image by DWSE(b=0) image and (2) multiplying this correction map $g(\vec{r})$ to all DWSE images with non-zero b value. The data acquisition time for the same number of b-values is reduced to half compared with that using a conventional DWSTE imaging technique.

The current method utilizes the entire diffusion-prepared magnetization, unlike the conventional DWSTE. Because the method uses a fixed mixing time and does not require $T_1$ correction, signal-b curve is significantly stable, particularly at the high-b region, say b>5000 s/mm², compared with the methods presented in previously reports[5,6,26].

Conventional diffusion MRI is generally used to measure low b DWI, usually b≤2500 s/mm², therefore spin-echo type acquisition is most efficient. At low b DWI, the signal change in DWI images is mostly caused by the diffusive motion of the extra cellular water molecules. However, because the water transport in and out of axons is very restricted perpendicular to the nerve fibers due to the layers of membranes wrapped around the axon that form the myelin sheath, DW imaging using a data acquisition technique with increased sensitivity to the water permeability is needed, such as DWSTE, to assess integrity of spinal cord fibers. Thus, DWSESTE is very useful technique, particularly for reducing the data acquisition time by acquiring additional diffusion-weighted spin-echo for low-b images.

As presented in FIGS. 6A-D, the signal-b curve on s set of DW images measured using the DWSESTE technique from human CSC clearly shows a double-exponential behavior, of which slow decaying curve at the high-b region represents the water permeability-related movement[4,19]. Hence, the method may be able to estimate the myelination or axonal damage in the white-matter and provide a powerful tool for quantitative evaluation of myelination of the spinal cord injuries in patients with Multiple Sclerosis (MS), degenerative cervical myelopathy, amyotrophic lateral sclerosis, and other toxic/metabolic myelopathies (such as subacute combined degeneration). For instance, in situations where a demyelinating lesion may induce axonal damage, leading to permanent disability, assessment of modalities that promote early remyelination is very critical. Therefore, a quantitative estimate of myelination will be particularly useful for monitoring remyelination therapies in MS, on which a handful experimental drugs are currently in development.

Water diffusion with no or weak barrier, such as in fluid or tissue with high permeability at the membrane, follows a Gaussian diffusion, therefore, both low-b DWSE and high-b DWSTE signals are supposed to follow a single-exponential decay. However, the signal-b curve is expected to differ with different diffusion time for white-matter, because of low permeability at the myelin sheath. The changes in the low-b DWI signal with short diffusion time ($\Delta_L$) and high-b DW signal with large diffusion time ($\Delta_H$) are sensitive to the water mobility in the extra-cellular space and water exchange across the myelin sheath, respectively. As shown in inserted plots of FIGS. 7A-B, difference between DWSE and DWSTE signals is negligible for the permeability up to 100 µm/s. Note that the permeability of the cellular membrane to the water molecule was reported as 30~700 µm/s in various cells[27] and 7~9 µm/s in bovine optic nerve[28]. The MCS indicates that the diffusion-related signal decays at the low-b DWI is dominated by water diffusion in the extra-cellular space, of which the probability function for the diffusion is close to a pure Gaussian function. Therefore, combining DWSE and DWSTE with RF and $T_1$ correction is acceptable. However, in real human imaging, different eddy-current at spin-echo and stimulated-echo positions may induce different geometric distortion on DWSE and DWSTE images, particularly at the DWI measured with large diffusion gradient. As a result, depending upon the surrounding tissue component, a specific imaging pixel may represent different physical pixel between DWSE and DWSTE.

Additionally, particularly, in b=0 DWSE and DWSTE that are used to generate a pixel-by-pixel correction function map $g(\vec{r}; \alpha, T_1)$, crusher gradient pairs sandwiching the second 90° RF pulse for DWSE and the second/third 90° RF pulses for DWSTE impose different b-factors with their ratio $$\left(\Delta_L - \frac{\delta}{3}\right) \Big/ \left(\Delta_H - \frac{\delta}{3}\right).$$

To remove the contribution from freshly recovered longitudinal magnetization, which can be flipped by the second and third RF pulses, an identical crusher gradient is applied before the second RF and immediately after the third RF pulse, of which the $0^{th}$ moment is small but large enough to dephase the spins within a single imaging voxel more than $2\pi$. In this pulse sequence, the diffusion gradient pulses also serve as the crusher gradients. A phase dispersion within a pixel dimension $\Delta x$ by a crusher area $A_{cr}$ is $\gamma_H A_{cr} \Delta x > 2\pi$, thus for $\Delta x = 1$ mm in readout direction, the area of a crusher gradient pulse must be $A_{cr} > 1/(4.257 \times 10^3/\text{s} \cdot \text{G} \cdot 0.1 \text{ cm}) = 2.35$ G/cm*ms=23.5 mT/m*ms. For slice-selective RF pulse duration of 4.0 ms and the same duration (18.4 ms) as diffusion gradient with 1.28 mT/m amplitude, the diffusion-weighting factors by these crusher gradients for DWSE and DWSTE are estimated as 4.6 and 30.6 s/mm². DWSE and DWSTE magnetizations decays 0.5% and 3.0% for D=1.0×

$10^{-3}$ mm$^2$/s, respectively. However, this difference in different diffusion weightings is also taken cared during the correction.

2D ss-DWSESTE can be used to rapidly estimate $T_1$ map by two single shot measurements; one with minimum TM for RF correction and another with increased TM, such as TM=400 ms. After correcting Bi inhomogeneity-related error using eq. (4), $T_1$ can be calculated by $T_{1(\vec{r})}=(\ln S_S E(\vec{r})-\ln S_S TE(\vec{r}))/TM^{13}$. The singleshot $T_1$ mapping may be used to improve the quantification of the MRI paramagnetic contrast agent for dynamic susceptibility contrast (DSC) MRI and dynamic contrast enhanced (DCE) MRI, as it is well-accepted that the change in $1/T_1$ is directly proportional to local concentration of the paramagnetic contrast agent over a wide range of concentration, as $\Delta(1/T_1)=1/T_1(C)-1/T_1(0)=r_1 C$. Here, $r_1$ and C are the relaxivity and local concentration of the contrast agent, respectively[29]. Another application of 2D ss-DWSESTE is acquiring the flipangle map by removing $T_1$ decay effect by minimizing TM to a few ms as in Shi's report[13]. In this application, small diffusion-weighting, say b=50 s/mm$^2$, may be applied to suppress bulk water signal, such as in CSF.

CONCLUSION

DW spin-echo and stimulated-echo (DWSESTE) images are successfully measured in a single acquisition pulse sequence in a half the imaging time compared with the conventional DWSTE technique, and combined for ultra-high-b DWI of human CSC imaging. The combined data set provides a reliable signal-b curves for further quantitative analysis of UHb-DWI method. The combined data can also be used to estimate the conventional DTI and DKI metrics. The data acquisition time, 6.5 min, using a routine coil is clinically acceptable for twenty-one 2D slices covering C1~T2 with maximum b of 9781 and 3240 s/mm$^2$ with 13 and 7 b-values for rDWI and aDWI, respectively. This imaging time can be reduced for specific situations, for example 3 min for seven rDWI and four aDWI encodings. This imaging can be accomplished with contemporary 3T MRI utilizing a commercially available head and neck coil.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A method comprising:
(a) applying, using at least one processing unit of an MRI system, a diffusion-weighting gradient during acquisition of diffusion-weighted imaging signals from a selected portion of a nervous system of a subject;
(b) obtaining, simultaneously from the MRI system, planar diffusion-weighted spin-echo (DWSE) imaging signals and planar diffusion-weighted stimulated-echo (DWSTE) imaging signals to provide a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value; and
(c) correcting, based on the first set of DWSE imaging signals and the first set of DWSTE imaging signals, a signal difference between the DWSE imaging signals and the DWSTE imaging signals.

Aspect 2: The method of aspect 1, wherein each set of imaging signals of the plurality of imaging signals are provided in respective pixel maps, wherein each pixel map of the respective pixel maps comprises a plurality of pixels associated with respective imaging signals at different locations within the selected portion of the nervous system of the subject, wherein correcting the signal difference between the DWSE imaging signals and the DWSTE imaging signals comprises:
calculating a pixel-by-pixel correction map comprising, for each pixel, a ratio of the imaging signals of the first set of DWSE imaging signals to the imaging signals of the first set of DWSTE imaging signals; and
multiplying at least one set of imaging signals by the pixel-by-pixel correction map.

Aspect 3: The method of aspect 2, wherein multiplying at least one set of imaging signals by the pixel-by-pixel correction map comprises multiplying all sets of imaging signals associated with DWSE by the pixel-by-pixel correction map.

Aspect 4: The method of aspect 2, wherein multiplying at least one set of imaging signals by the pixel-by-pixel correction map comprises multiplying all sets of imaging signals associated with DWSTE by the pixel-by-pixel correction map.

Aspect 5: The method of any one of the preceding aspects, wherein the high-b-value is above 3,000 s/mm$^2$.

Aspect 6: The method of aspect 5, wherein the plurality of sets of imaging signals comprise a plurality of sets of DWSTE imaging signals associated with b-values above 3,000 s/mm2.

Aspect 7: The method of any one of the preceding aspects, wherein the method does not comprise a time correction.

Aspect 8: The method of any one of the preceding aspects, wherein the method comprises using a fixed mixing time.

Aspect 9: The method of aspect 8, wherein the fixed mixing time is about 100 ms.

Aspect 10: The method of any one of the preceding aspects, wherein obtaining, simultaneously from the MRI system, planar diffusion-weighted spin-echo (DWSE) imaging signals and planar diffusion-weighted stimulated-echo (DWSTE) imaging signals comprises obtaining, simultaneously from the MRI system, planar diffusion-weighted spin-echo (DWSE) imaging signals and planar diffusion-weighted stimulated-echo (DWSTE) imaging signals with a reduced field-of-view.

Aspect 11: The method of aspect 10, wherein the reduced field of view comprises using two adiabatic full passage (AFP) pulses with a crusher gradient.

Aspect 12: The method of any one of the preceding aspects, wherein the selected portion of the nervous system of the subject comprises white matter of a spinal cord of the subject.

Aspect 13: The method of aspect 12, further comprising evaluating myelination or axonal damage in the white-matter based on the planar imaging.

Aspect 14: The method of any one of the preceding aspects, wherein the diffusion-weighted imaging signals comprise radial diffusion-weighted imaging signals.

Aspect 15: The method of any one of the preceding aspects, wherein the diffusion-weighted imaging signals comprise axial diffusion-weighted imaging signals.

Aspect 16: A system comprising:

a magnetic resonance imaging system that is configured to:

apply a diffusion-weighting gradient during acquisition of diffusion-weighted imaging signals from a selected portion of a nervous system of a subject, obtain, simultaneously from the MRI system, planar diffusion-weighted spin-echo (DWSE) imaging signals and planar diffusion-weighted stimulated-echo (DW-STE) imaging signals to provide a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value; and a memory; and at least one processor in communication with the memory, wherein the memory comprises instructions that, when executed by the at least one processor, cause the processor to correct, based on the first set of DWSE imaging signals and the first set of DWSTE imaging signals, a signal difference between the DWSE imaging signals and the DWSTE imaging signals.

Aspect 17: The system of aspect 16, wherein the memory comprises instructions that, when executed by the at least one processor, cause the processor to:

calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

Aspect 18: The system of aspect 16 or aspect 17, wherein the high b-value diffusion-weighting gradient comprises at least one b-value above 3,000 s/mm2.

Aspect 19: The system of any one of aspect 16-18, wherein the magnetic resonance imaging system uses a fixed mixing time.

Aspect 20: The system of aspect 19, wherein the fixed mixing time is about 100 ms.

Aspect 21: A computing device comprising:

a memory; and at least one processor in communication with the memory, wherein the memory comprises instructions that, when executed by the at least one processor, cause the processor to:

receive simultaneously obtained planar diffusion-weighted spin-echo (DWSE) imaging signals and planar diffusion-weighted stimulated-echo (DW-STE) imaging signals that are provided as a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value; and correct, based on the first set of DWSE imaging signals and the first set of DWSTE imaging signals, a signal difference between the DWSE imaging signals and the DWSTE imaging signals.

Aspect 22: The system of aspect 21, wherein the memory comprises instructions that, when executed by the at least one processor, cause the processor to:

calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

Aspect 23: The system of aspect 21 or aspect 22, wherein the high-b-value is above 3,000 s/mm$^2$.

Although the foregoing invention has been described in some detail by way of illustration and example for purposes of clarity of understanding, certain changes and modifications may be practiced within the scope of the appended claims.

REFERENCES

The following references, which are cited in the preceding disclosure, are hereby incorporated by reference herein.

(1) Merboldt, K.; Hanicke, W.; Gyngell, M.; Frahm, J.; Bruhn, H. Rapid NMR Imaging of Molecular Self-Diffusion Using a Modified CE-Fast Sequence. *J Magn. Reson. Imag.* 1989, 82, 115.

(2) Merboldt, K. D.; Hanicke, W.; Bruhn, H.; Gyngell, M. L.; Frahm, J. Diffusion Imaging of the Human Brain in Vivo Using High-Speed STEAM MRI. *Magn Reson Med* 1992, 23 (1), 179-192.

(3) Farrell, J. A.; Smith, S. A.; Gordon-Lipkin, E. M.; Reich, D. S.; Calabresi, P. A.; van Zijl, P. C. High B-Value q-Space Diffusion-Weighted MRI of the Human Cervical Spinal Cord in Vivo: Feasibility and Application to Multiple Sclerosis. *Magn Reson Med* 2008, 59 (5), 1079-1089.

(4) Sapkota, N.; Yoon, S.; Thapa, B.; Lee, Y.; Bisson, E.; Bowman, B.; Miller, S.; Shah, L.; Rose, J.; Jeong, E. Characterization of Spinal Cord White Matter by Suppressing Signal from Hindered Space. A Monte Carlo Simulation and an Ex Vivo Ultrahigh-b Diffusion-Weighted Imaging Study. *J. Magn. Reson.* 2016, 272, 53-59.

(5) Thapa, B.; Sapkota, N.; Lee, Y.; Jeong, K.; Rose, J.; Shah, L. M.; Bisson, E.; Jeong, E. K. Ultra-High-b Radial Diffusion-Weighted Imaging (UHb-RDWI) of Human Cervical Spinal Cord. *J. Magn. Reson. Imaging* 2019, 49 (1), 204-211.

(6) Jeong, K. E.; Shah, L. M.; Lee, S. Y.; Thapa, B.; Sapkota, N.; Bisson, E. F.; Carlson, N. G.; Jeong, E. K.; Rose, J. W. High-b Diffusivity of MS Lesion in Cervical Spinal Cord Using Ultrahigh-b DWI (UHb-DWI). *NeuroImage:Clinical* 2021, 30, 102619.

(7) Sapkota, N.; Shi, X.; Shah, L. M.; Bisson, E. F.; Rose, J.; Jeong, E. Two-Dimensional Single-Shot Diffusion-Weighted Stimulated EPI with Reduced FOV for Ultra-high-b Radial Diffusion-Weighted Imaging of Spinal Cord. *Magn. Reson. Med.* 2016, 77 (6), 2167-2173.

(8) Slichter, C. P. *Principles of Magnetic Resonance,* 3rd ed.; Springer-Verlag: Heidelberg, Germany, 1990.

(9) Haacke, E. M.; Thompson, M. R.; Brown, R. W. *Magnetic Resonance Imaging, Physical Principles and Sequence Design*; Wiley-Liss, 1999.

(10) Haase, A.; Frahm, J.; Matthaei, D.; Hanicke, W.; Bomsdorf, H.; Kunz, D.; Tischler, R. MR Imaging Using Stimulated Echoes (STEAM). *Radiology* 1986, 160 (3), 787-790.

(11) Bornert, P.; Jensen, D. Single-Shot-Double-Echo EPI. *Magn Reson Imaging* 1994, 12 (7), 1033-1038.

(12) Franconi, F.; Sonier, C. B.; Seguin, F.; Le Pape, A.; Akoka, S. Acquisition of Spin Echo and Stimulated Echo by a Single Sequence: Application to MRI of Diffusion. *Magn. Reson. Imaging* 1994, 12 (4), 605-611. https://doi.org/10.1016/0730-725X(94)92455-4.

(13) Shi, X.; Jeong, E. Single-Shot T1 Mapping Using Simultaneous Acquisitions of Spin- and Stimulated-Echo-Planar Imaging (2D Ss-SESTEPI). *Magn Reson Med* 2010, 64 (3), 734-742.

(14) Jeong, E. K.; Kholmovski, E. G.; Parker, D. L. High-Resolution DTI of a Localized Volume Using 3D Single-Shot Diffusion-Weighted STimulated Echo-Planar Imaging (3D Ss-DWSTEPI). *Magn Reson Med* 2006, 56 (6), 1173-1181.

(15) Jeong, E. K.; Guo, J.; Kholmovski, E. G.; Parker, D. L. High-Resolution DTI with 2D Interleaved Multislice Reduced FOV Single-Shot Diffusion-Weighted EPI (2D Ss-RFOV-DWEPI). *Magn Reson Med* 2005, 54 (6), 1575-1579.

(16) Skinner, N. P.; Kurpad, S. N.; Schmit, B. D.; Tugan Muftuler, L.; Budde, M. D. Rapid in Vivo Detection of Rat Spinal Cord Injury with Double-Diffusion-Encoded Magnetic Resonance Spectroscopy. *Magn. Reson. Med.* 2017, 77 (4), 1639-1649.

(17) Tabesh, A.; Jensen, J. H.; Ardekani, B. A.; Helpern, J. A. Estimation of Tensors and Tensor-Derived Measures in Diffusional Kurtosis Imaging. *Magn. Reson. Med.* 2011, 65 (3), 823-836. https://doi.org/10.1002/mrm.22655.

(18) Chuhutin, A.; Hansen, B.; Wlodarczyk, A.; Owens, T.; Shemesh, N.; Jespersen, S. N. Diffusion Kurtosis Imaging Maps Neural Damage in the EAE Model of Multiple Sclerosis. *Neuroimage* 2020, 208, 116406. https://doi.org/10.1016/j.neuroimage.2019.116406.

(19) Jeong, K. E.; Lee, S. Y. J.; Yeom, S. K.; Carlson, N. G.; Shah, L. M.; Rose, J. W.; Jeong, E. K. Ultrahigh-b DWI (UHb-DWI) for Quantitative Evaluation of Myelination in Shiverer Mouse Spinal Cord. *Magn Reson Med* 2021, in-print, PMID: 34418157 DOI: 10.1002/mrm.28978. https://doi.org/10.1002/mrm.28978.

(20) Lovas, G.; Szilágyi, N.; Majtényi, K.; Palkovits, M.; Komoly, S. Axonal Changes in Chronic Demyelinated Cervical Spinal Cord Plaques. *Brain* 2000, 123, 308-317. https://doi.org/10.1093/brain/123.2.308.

(21) Hasan, K. M.; Lincoln, J. A.; Nelson, F. M.; Wolinsky, J. S.; Narayana, P. A. Lateral Ventricular Cerebrospinal Fluid Diffusivity as a Potential Neuroimaging Marker of Brain Temperature in Multiple Sclerosis: A Hypothesis and Implications. *Magn. Reson. Imaging* 2015, 33 (3), 262-269. https://doi.org/10.1016/j.mri.2014.11.002.

(22) Holz, M.; Heil, S. R.; Sacco., A. Temperature-Dependent Self-Diffusion Coefficients of Water and Six Selected Molecular Liquids for Calibration in Accurate 1H NMR PFG Measurements. *Phys. Chem. Chem. Phys.* 2000, 2, 4740-4742. https://doi.org/10.1039/B005319He.

(23) Tofts, P. S.; Lloyd, D.; Clark, C. A.; Barker, G. J.; Parker, G. J. M.; McConville, P.; Baldock, C.; Pope, J. M. Test Liquids for Quantitative MRI Measurements of Self-Diffusion Coefficient in Vivo. *Magn Reson Med* 2000, 43 (3), 368-374.

(24) Wilm, B. J.; Svensson, J.; Henning, A.; Pruessmann, K. P.; Boesiger, P.; Kollias, S. S. Reduced Field-of-View MRI Using Outer Volume Suppression for Spinal Cord Diffusion Imaging. *Magn Reson Med* 2007, 57 (3), 625-630.

(25) Saritas, E. U.; Cunningham, C. H.; Lee, J. H.; Han, E. T.; Nishimura, D. G. DWI of the Spinal Cord with Reduced FOV Single-Shot EPI. *Magn Reson Med* 2008, 60 (2), 468-473.

(26) Sapkota, N.; Shi, X.; Shah, L. M.; Bisson, E. F.; Rose, J. W.; Jeong, E. K. E. K.; Guo, J.; Kholmovski, E. G.; Parker, D. L. High-Resolution DTI with 2D Interleaved Multislice Reduced FOV Single-Shot Diffusion-Weighted EPI (2D Ss-RFOV-DWEPI). *Magn Reson Med.* 2016, pp 1575-1579. https://doi.org/10.1002/mrm.26302.

(27) Dick, D. The Permeability Coefficient of Water in the Cell Membrane and the Diffusion Coefficient in the Cell Interior. *J. Theor. Biol.* 1964, 7, 504-531.

(28) Stanisz, G. J.; Szafer, A.; Wright, G. A.; Henkelman, R. M. An Analytical Model of Restricted Diffusion in Bovine Optic Nerve. *Magn. Reson. Med.* 1997, 37 (1), 103-111.

(29) Nicolle, G. M.; Tóth, É.; Schmitt-Willich, H.; Radüchel, B.; Merbach, A. E. The Impact of Rigidity and Water Exchange on the Relaxivity of a Dendritic MRI Contrast Agent. *Chem. —A Eur. J.* 2002, 8 (5), 1040-1048. https://doi.org/10.1002/1521-3765(20020301)8:5<1040::AID-CHEM1040>3.0.CO; 2-D.

What is claimed is:

1. A method comprising:

(a) applying, using at least one processing unit of an MRI system, a diffusion-weighting gradient during acquisition of diffusion-weighted imaging signals from a selected portion of a nervous system of a subject;

(b) obtaining, simultaneously from the MRI system, planar diffusion-weighted spin-echo (DWSE) imaging signals and planar diffusion-weighted stimulated-echo (DWSTE) imaging signals to provide a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value, wherein the high-b-value is at or above 3,000 s/mm$^2$; and (c) correcting, based on the first set of DWSE imaging signals and the first set of DWSTE imaging signals, a signal difference between the DWSE imaging signals and the DWSTE imaging signals.

2. The method of claim 1, wherein each set of imaging signals of the plurality of imaging signals are provided in respective pixel maps, wherein each pixel map of the respective pixel maps comprises a plurality of pixels associated with respective imaging signals at different locations within the selected portion of the nervous system of the subject, wherein correcting the signal difference between the DWSE imaging signals and the DWSTE imaging signals comprises:

calculating a pixel-by-pixel correction map comprising, for each pixel, a ratio of the imaging signals of the first set of DWSE imaging signals to the imaging signals of the first set of DWSTE imaging signals; and multiplying at least one set of imaging signals by the pixel-by-pixel correction map.

3. The method of claim 2, wherein multiplying at least one set of imaging signals by the pixel-by-pixel correction map comprises multiplying all sets of imaging signals associated with DWSE by the pixel-by-pixel correction map.

4. The method of claim 2, wherein multiplying at least one set of imaging signals by the pixel-by-pixel correction map comprises multiplying all sets of imaging signals associated with DWSTE by the pixel-by-pixel correction map.

5. The method of claim 1, wherein the plurality of sets of imaging signals comprise a plurality of sets of DWSTE imaging signals associated with b-values above 3,000 s/mm².

6. The method of claim 1, wherein the method does not comprise a time correction.

7. The method of claim 1, wherein the method comprises using a fixed mixing time.

8. The method of claim 7, wherein the fixed mixing time is within 15% of 100 ms.

9. The method of claim 1, wherein obtaining, simultaneously from the MRI system, planar diffusion-weighted spin-echo (DWSE) imaging signals and planar diffusion-weighted stimulated-echo (DWSTE) imaging signals comprises obtaining, simultaneously from the MRI system, planar diffusion-weighted spin-echo (DWSE) imaging signals and planar diffusion-weighted stimulated-echo (DWSTE) imaging signals with a reduced field-of-view.

10. The method of claim 9, wherein the reduced field of view comprises using two adiabatic full passage (AFP) pulses with a crusher gradient.

11. The method of claim 1, wherein the selected portion of the nervous system of the subject comprises white matter of a spinal cord of the subject.

12. The method of claim 11, further comprising evaluating myelination or axonal damage in the white-matter based on the planar imaging.

13. The method of claim 1, wherein the diffusion-weighted imaging signals comprise radial diffusion-weighted imaging signals.

14. The method of claim 1, wherein the diffusion-weighted imaging signals comprise axial diffusion-weighted imaging signals.

15. A system comprising:

a magnetic resonance imaging system that is configured to:

apply a diffusion-weighting gradient during acquisition of diffusion-weighted imaging signals from a selected portion of a nervous system of a subject, obtain, simultaneously from the MRI system, planar diffusion-weighted spin-echo (DWSE) imaging signals and planar diffusion-weighted stimulated-echo (DWSTE) imaging signals to provide a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value, wherein the high-b-value is at or above 3,000 s/mm²; and a memory; and at least one processor in communication with the memory, wherein the memory comprises instructions that, when executed by the at least one processor, cause the processor to correct, based on the first set of DWSE imaging signals and the first set of DWSTE imaging signals, a signal difference between the DWSE imaging signals and the DWSTE imaging signals.

16. The system of claim 15, wherein the memory comprises instructions that, when executed by the at least one processor, cause the processor to:

calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

17. The system of claim 15, wherein the high b-value diffusion-weighting gradient comprises at least one b-value above 3,000 s/mm².

18. A computing device comprising:

a memory; and at least one processor in communication with the memory, wherein the memory comprises instructions that, when executed by the at least one processor, cause the processor to:

receive simultaneously obtained planar diffusion-weighted spin-echo (DWSE) imaging signals and planar diffusion-weighted stimulated-echo (DWSTE) imaging signals that are provided as a plurality of sets of imaging signals, wherein the plurality of sets of imaging signals comprise a first set of DWSE imaging signals associated with a first low-b-value that is at or near zero, a first set of DWSTE imaging signals associated with a second low-b-value that is at or near zero, and a second set of DWSTE signals that are associated with a high-b-value, wherein the high-b-value is at or above 3,000 s/mm²; and correct, based on the first set of DWSE imaging signals and the first set of DWSTE imaging signals, a signal difference between the DWSE imaging signals and the DWSTE imaging signals.

19. The system of claim 18, wherein the memory comprises instructions that, when executed by the at least one processor, cause the processor to:

calculate a pixel-by-pixel correction map comprising, for each pixel, a ratio of the imaging signals of the first set of DWSE imaging signals to the imaging signals of the first set of DWSTE imaging signals; and multiply at least one set of imaging signals by the pixel-by-pixel correction map.

20. The method of claim 1, wherein each of the second low-b-values is less than 100 s/mm².

* * * * *